(12) United States Patent
Emerson et al.

(10) Patent No.: US 6,797,816 B2
(45) Date of Patent: Sep. 28, 2004

(54) IDENTIFICATION AND CLONING OF A NEW SUBFAMILY OF SULFATASES AND FUNCTIONAL EMBRYONIC TECHNIQUES FOR CHARACTERIZATION OF SUCH PROTEINS

(75) Inventors: Charles P. Emerson, Bala Cynwyd, PA (US); Gurtej Kaur Dhoot, London (GB)

(73) Assignee: Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 10/389,532

(22) Filed: Mar. 13, 2003

(65) Prior Publication Data

US 2003/0158084 A1 Aug. 21, 2003

Related U.S. Application Data

(63) Continuation of application No. 09/668,673, filed on Sep. 22, 2000, now Pat. No. 6,562,956.
(60) Provisional application No. 60/155,738, filed on Sep. 23, 1999.

(51) Int. Cl.[7] .......................... C07H 21/04; C12N 9/16; C12N 1/20; C12N 15/00
(52) U.S. Cl. ................... 536/23.2; 435/196; 435/252.3; 435/320.1; 530/350
(58) Field of Search ........................ 536/23.2; 435/196, 435/252.3, 320.1; 530/350

(56) References Cited

PUBLICATIONS

Adams et al. Nature 377 (6547 Suppl), 3–174 (1995).*
Adams et al., "Initial assessment of human gene diversity and expression patterns based upon 83 million nucleotides of cDNA sequence", Nature 1995 377:3–174.

Kikuno et al., "Prediction of the Coding Sequences of Unidentified Human Genes. XIV. The Complete Sequences of 100 New cDNA Clones from Brain Which Code for Large Proteins in vitro", DNA Res. 1999 6:197–205.

Robertson et al., "Chromosomal localization of the gene for human glucosamine–6–sulphatase to 12q14", Hum. Genet. 1988 79 (2) :175–178.

Robertson et al., "Human Glucosamine–6–Sulfatase cDNA Reveals Homology with Steroid Sulfatase", Biochem. Biophys. Res. Commun. 1988 157 (1) 218–224.

Robertson et al., "A cDNA clone for human glucosamine–6–sulphatase reveals differences between arylsulphatases and non–arylsulphatases", Biochem. J. 1992 288:539–544.

* cited by examiner

Primary Examiner—Tekchand Saidha
(74) Attorney, Agent, or Firm—Licata & Tyrrell P.C.

(57) ABSTRACT

Nucleic acid sequences encoding members of a new subfamily of sulfatases and polypeptides encoded thereby are provided. Compositions and methods of modulating sulfatases of this new subfamily to modify growth properties and differentiation of cells, as well as the ability of cells to prevent viral entry and to prevent recruitment of lymphocytes to a site of inflammation are also provided. The compositions and methods are useful in treating cancer and inhibiting metastases, promoting differentiation of stem cells into muscle, neural and renal cells and inhibiting viral infection and inflammation. In addition, functional embryonic techniques for identification and characterization of developmental regulatory genes such as these sulfatases are provided.

2 Claims, 1 Drawing Sheet

SEQUENCE LISTING

<160> NUMBER OF SEQ ID NOS: 22

<210> SEQ ID NO 1
<211> LENGTH: 5769
<212> TYPE: DNA
<213> ORGANISM: quails

<400> SEQUENCE: 1
ggcacgagct cagccctata gtttcagccc ttgtctctgc ctccagctcc ttaagagcca 60
cccagcccca gcgatcggat tgggcagccc gccttgacac accactgtgc tgagtgcttg 120
aggacgtgtt tcaacagatg gttggggtta gtgtgtgtca tcacactcga gtggggatta 180
gggcagagag gcagcccggc tggagctgtg tggtcttccc caagtgggaa ctgcgagcaa 240
aagaagaagc acctagcttt gggggagaag agagaggaat cctctccagc agctcagagg 300
ggaaaataaa accctcactc tttattcagc cagaaaagaa agactgatct ggggaagagt 360
ggaaaaacaa tgacaatata tctttcttgc ataagacaaa ggtgttgcct acaataaatt 420
cactgagcaa gaaatacaga cttctgtcca gtgctatgaa aattaaccaa ggcacattaa 480
cttcaggaaa tcttcaaagg acagaggaag aagctgtact gaacagtcct ggagactctg 540
aagcacaggc acagcgctga ggtctttgac tgacagacct tctgctttct ccttcttgca 600
gggctcctcc tacagatgtt ctgaacacgt ctgcatccca gcaattttgt actgcaccca 660
ggtcttgaaa actggagttc aggcacttct ggattgggtt tgtgttgttt ttttttttca 720
ttgaaatact ggaactacta tgaagacctc ttggtttgca ctcttcttgg cagtgctcag 780
tactgaactg ctgacaagtc attcttccac tctcaagtcc ctgaggttca gaggccgtgt 840
gcagcaagag agaaaaaata tcagaccaaa tatcatcctt gtgctcacag atgaccaaga 900
tgtggagcta gggtccttac aagtgatgaa caaaaccaga cggattatgg agaatggagg 960
ggcatccttc atcaatgcct tcgtaacaac cccgatgtgc tgcccatcac gttcctccat 1020
gctgactgga aagtatgtgc acaaccacaa catatacacc aacaatgaaa actgctcttc 1080
tccctcctgg caggccactc acgagccacg cactttcgcc gtgtatctga ataacactgg 1140
gtatcgaaca gctttttttg ggaaatacct caatgaatac aatggcagct acatccctcc 1200
tgggtggaga gagtgggttg gattagtgaa gaactctcgc ttctataatt acaccatttc 1260
tcgcaatggt aacaaagaga agcatggatt tgattatgca aaggactact tcacagacct 1320
aatcactaat gagagcatta attacttcag aatgtccaag aggatatacc cacataggcc 1380
cataatgatg gtcatcagcc atgctgcgcc tcatggccct gaggattcgg ccccacagtt 1440
ctcagagctc taccccaacg cttcacagca tatcaccccc agctataact atgcaccaaa 1500

```
catggataag cactggatca tgcagtacac ggggcccatg ctgcctatcc acatggagtt    1560
tacaaacgtc ttgcaacgca agagacttca gaccctgatg tcagttgatg actctatgga    1620
aagattatac caaatgcttg cagaaatggg agagctggag aatacctaca ttatttacac    1680
agctgaccat ggttaccata ttgggcagtt tggactggtc aaggggaagt caatgccata    1740
tgactttgat attcgagttc ctttctttat tcgtggtcca agtgtagagc caggatctgt    1800
agtgcctcag atagttctga atattgatct tgcaccaaca attctggata ttgcaggact    1860
tgacacacct ccagatatgg atggcaaatc tgtcctaaag cttctagact tggagagacc    1920
aggaaatagg tttcgaacaa acaagaagac caaaatctgg cgtgacacat tcctggtgga    1980
aagaggcaaa tttctgcgca aaaagagga agctaacaaa acactcagc aatctaatca    2040 actgccaaag tatgagaggg taaagaatt atgccaacaa gcgagatacc agacagcctg    2100
tgaacaacca ggacagaagt ggcagtgcac agaagatgct tctggcaagc ttcgaattca    2160
caagtgcaag gtatcagtg acatcctggc catcaggaaa aggacccgca gcatccactc    2220
caggggatay agtggtaaag ataaggactg caactgtgga gacaccgatt tccgaaacag    2280
caggacccaa agaaaaaatc aaaggcagtt tctgagaaac cccagtgcgc aaaaatacaa    2340
accacgtttt gttcacactc gccaaacccg gtccttgtca gtggaatttg aaggtgaaat    2400
atatgacata aacctggaag aggaagaact gcaggtgtta agaccagaa gtatcaccaa    2460 acgtcacaat gctgaaaatg acaaaaaagc agaggaaact gatggtgctc ctggtgacac    2520
gatggttgct gatggcactg atgttatagg tcaacccagt tctgtcagag tgacrcacaa    2580 gtgtttatt cttccaaatg acactattcr ctgtgagagg gagctgtacc aatctgccag    2640
agcctggaag gaccacaagg cttacatcga taaggagatt gaagctctcc aggacaaaat    2700
caagaatttg agggaagtta gaggacacct aaaaagaaga aaaccagacg aatgtgactg    2760
tactaaacag agctactaca acaaagagaa aggcgtaaag acccaagaga aaatcaagag    2820
ccatctacat cccttcaaag aagcagcaca ggaggtagac agcaaactgc agctgttcaa    2880
agagaatcgc agaaggaaga aggaaagaaa gggaaaaaag cgccagaaga argggggatga    2940 gtgtagcctt cctggactga catgtttac tcatgacaat aaccattggc aaactgcacc    3000
tttctggaac ttgggatctt tctgtgcttg cacaagctca ataacaaca cttactggtg    3060 tttgcgaaca gtgaatgaca cccacaattt tctcttttgt gaatttgcaa ctggcttctt    3120
ggaatwcttt gatatgaaca ctgaccccta tcagctgaca aataccgtac atacagtgga    3180
aagaggcatt ttaaatcaat tacatgtaca gttaatggaa ttacgaagtt gtcaaggtta    3240
taagcagtgc aatccgaggc cgaagggact tgaaacagga aataaagatg gaggaagcta    3300
tgatccacac agaggacagt tatgggatgg atggaaggc taacctgccc agtttcactg    3360
gtgatgtcaa ctggcaagga ctggaaaatt tgtacagagt gaataaaagt gtatatgaac    3420
acagatacaa ctatagactt agtctggctg actggactaa ttacttgaag gatgtagata    3480
gaatgtttgc actgctgaac agttactacc agcaaaataa acagacaag gctaacactg    3540 ctcaaagcaa cagggatgga gatgaatcat ctacatcaac ctcagcagaa atgtcttctg    3600
cagaagaggc aagtggcctg actggagaag aattggagct tattgtgcca acagactttg    3660
cagccctagc tttgagcacc atgaatttaa gtcaggagag aaaacttgaa ttaaacaatg    3720
atattcctga aaaagtagt ttgaatgacg cacactggag aaataatcaa gctgaaaaat    3780
ggatggwgga taaagaatca gaacgttttg atatggattt cagtgaaat ggtttgatac    3840 agttggagtc ccggcatggc ttcatgctac agcccatcag cattcctcaa aaagacaytc    3900
```

```
atcaggacac tgatgctatg agagacatat ttggagatca aatgtatctt cctgtgaggt    3960
ccgatcaacc tgttgttcat caggctgtaa atgtatccat tagagattca tccatcagta    4020
cccagaaaac aggaacgttt ttgaaaaaaa caaaacagag tcttagaggg gaaacttcac    4080
aagtcctaaa catagaaggc agcgcctcat ctccactctc cttgggttag atcaagttgc    4140
agattgttaa atacattctc cttttttctt attaccagaa ttataaaggc aatcatgaca    4200
actgacattc catattgast gtagatacaa tttgcagcta aattaagacc agttcagtat    4260
ttgtctgtgt gtatttttatt cacacgcaca catacrtact ttcacagtga ttcrctacac    4320
tggaaagcag gatttccagc ttttaatgaa agaaaaagt gttaactttc taatgcagca    4380
gcacattctc tataagctaa gatttctttg acaaggatgt tcaagtgact ttctctattt    4440
ccagatgatc ccaccatgaa tgaatgtttc agtccaccca atctgtctgc ataatgtgtt    4500
tctgataaat tattttaacc actggaaatt cctaatgcca cactttcgag taaaacgatg    4560
ttgcactttt aaaatctgta tgccatacca tttatgaatc taataactta cctgttctta    4620
gtttgttcgt tgactaatgt aattgtgaaa ccaataaata gattgacagg aaagagataa    4680
ccagcatgga ctgtggaaat agattgaata tcattttagc aaaaatattg catgtttttg    4740
ttactttgat tgaattaaat ttgctctcag aaaggtatgg ctaatacttg ttaactagag    4800
gaggatttgt ttaaattgga ttgtttccct atatacgaca ttgtcagtat taaaattaca    4860
tgagtttgtt kgkttttttt wttaactttt ttttttwtt ttatctaata ctggtagaaa    4920
ggcttgtgtc aattcatata tacttctgtc acaagatctg attttatta gcctgaatga    4980 taccttgaaa acattctttt catttcgaga cttcaatttg tggtgttgtt ttgaacagtc    5040
attaaaggga atgataaaat catgttagat ttacattatt ctagatgcac atggggtaaa    5100
aagtagtagc ttagatagtt tttgttgttg tattgctctg aagttttttc ttgaacttta    5160
tcaaacttta aattttataa agtataaaaa aaacacaaa aaacacaaac acaaaaactt    5220
caaaatctgt actactagaa actatctttt tttgttttt aataaattca aagtcattag    5280
cacaacacca ccaaacgaga attacctcaa acagatgaa ttccacagca tccagttctt    5340
gggagtgttt cctatctgtt ccgtcttaat tagtgtagtg agtgttttgg ggctactgca    5400
agcactgcag gttaaactta cgttcatcac attgtacttt cagttgaaac aagattgttt    5460
tagtaggatt ttaataattt taagaagcgg tcttttgat ggactctgta catatgttaa    5520
aattaactag ctctttgtct gatgtatgtg tcacgggctg attgatagaa gaagcgtatt    5580
tatggtcatg aatgaagcta ttatttgtac ataggtttca agttactagg ataccagctg    5640 tgttttaaa acttgtataa tacttctgtg atacttttat agaacaattc tggcttcggg    5700
aaagtctaga agcaatattt cttgaaataa aaagtgtttt actttacctg ccaaaaaaaa    5760
aaaaaaaaa                                                             5769
```

<210> SEQ ID NO 2
<211> LENGTH: 867
<212> TYPE: PRT
<213> ORGANISM: quails

<400> SEQUENCE: 2

```
Met Lys Thr Ser Trp Phe Ala Leu Phe Leu Ala Val Leu Ser Thr Glu
 1               5                   10                  15

Leu Leu Thr Ser His Ser Ser Thr Leu Lys Ser Leu Arg Phe Arg Gly
            20                  25                  30
```

-continued

```
Arg Val Gln Gln Glu Arg Lys Asn Ile Arg Pro Asn Ile Ile Leu Val
             35                  40                  45
Leu Thr Asp Asp Gln Asp Val Glu Leu Gly Ser Leu Gln Val Met Asn
 50                  55                  60
Lys Thr Arg Arg Ile Met Glu Asn Gly Gly Ala Ser Phe Ile Asn Ala
 65                  70                  75                  80
Phe Val Thr Thr Pro Met Cys Cys Pro Ser Arg Ser Ser Met Leu Thr
                 85                  90                  95
Gly Lys Tyr Val His Asn His Asn Ile Tyr Thr Asn Asn Glu Asn Cys
                100                 105                 110
Ser Ser Pro Ser Trp Gln Ala Thr His Glu Pro Arg Thr Phe Ala Val
            115                 120                 125
Tyr Leu Asn Asn Thr Gly Tyr Arg Thr Ala Phe Phe Gly Lys Tyr Leu
130                 135                 140
Asn Glu Tyr Asn Gly Ser Tyr Ile Pro Pro Gly Trp Arg Glu Trp Val
145                 150                 155                 160
Gly Leu Val Lys Asn Ser Arg Phe Tyr Asn Tyr Thr Ile Ser Arg Asn
                165                 170                 175
Gly Asn Lys Glu Lys His Gly Phe Asp Tyr Ala Lys Asp Tyr Phe Thr
            180                 185                 190
Asp Leu Ile Thr Asn Glu Ser Ile Asn Tyr Phe Arg Met Ser Lys Arg
            195                 200                 205
Ile Tyr Pro His Arg Pro Ile Met Met Val Ile Ser His Ala Ala Pro
210                 215                 220
His Gly Pro Glu Asp Ser Ala Pro Gln Phe Ser Glu Leu Tyr Pro Asn
225                 230                 235                 240
Ala Ser Gln His Ile Thr Pro Ser Tyr Asn Tyr Ala Pro Asn Met Asp
                245                 250                 255
Lys His Trp Ile Met Gln Tyr Thr Gly Pro Met Leu Pro Ile His Met
            260                 265                 270
Glu Phe Thr Asn Val Leu Gln Arg Lys Arg Leu Gln Thr Leu Met Ser
            275                 280                 285
Val Asp Asp Ser Met Glu Arg Leu Tyr Gln Met Leu Ala Glu Met Gly
290                 295                 300
Glu Leu Glu Asn Thr Tyr Ile Ile Tyr Thr Ala Asp His Gly Tyr His
305                 310                 315                 320
Ile Gly Gln Phe Gly Leu Val Lys Gly Lys Ser Met Pro Tyr Asp Phe
                325                 330                 335
Asp Ile Arg Val Pro Phe Phe Ile Arg Gly Pro Ser Val Glu Pro Gly
            340                 345                 350
Ser Val Val Pro Gln Ile Val Leu Asn Ile Asp Leu Ala Pro Thr Ile
            355                 360                 365
Leu Asp Ile Ala Gly Leu Asp Thr Pro Pro Asp Met Asp Gly Lys Ser
370                 375                 380
Val Leu Lys Leu Leu Asp Leu Glu Arg Pro Gly Asn Arg Phe Arg Thr
385                 390                 395                 400
Asn Lys Lys Thr Lys Ile Trp Arg Asp Thr Phe Leu Val Glu Arg Gly
                405                 410                 415
Lys Phe Leu Arg Lys Lys Glu Ala Asn Lys Asn Thr Gln Gln Ser
            420                 425                 430
Asn Gln Leu Pro Lys Tyr Glu Arg Val Lys Glu Leu Cys Gln Gln Ala
            435                 440                 445
Arg Tyr Gln Thr Ala Cys Glu Gln Pro Gly Gln Lys Trp Gln Cys Thr
```

-continued

```
            450                 455                 460
Glu Asp Ala Ser Gly Lys Leu Arg Ile His Lys Cys Lys Val Ser Ser
465                 470                 475                 480

Asp Ile Leu Ala Ile Arg Lys Arg Thr Arg Ser Ile His Ser Arg Gly
                485                 490                 495

Tyr Ser Gly Lys Asp Lys Asp Cys Asn Cys Gly Asp Thr Asp Phe Arg
                500                 505                 510

Asn Ser Arg Thr Gln Arg Lys Asn Gln Arg Gln Phe Leu Arg Asn Pro
                515                 520                 525

Ser Ala Gln Lys Tyr Lys Pro Arg Phe Val His Thr Arg Gln Thr Arg
530                 535                 540

Ser Leu Ser Val Glu Phe Glu Gly Ile Tyr Asp Ile Asn Leu Glu
545                 550                 555                 560

Glu Glu Glu Leu Gln Val Leu Lys Thr Arg Ser Ile Thr Lys Arg His
                565                 570                 575

Asn Ala Glu Asn Asp Lys Lys Ala Glu Thr Asp Gly Ala Pro Gly
                580                 585                 590

Asp Thr Met Val Ala Asp Gly Thr Asp Val Ile Gly Gln Pro Ser Ser
                595                 600                 605

Val Arg Val Thr His Lys Cys Phe Ile Leu Pro Asn Asp Thr Ile Arg
                610                 615                 620

Cys Glu Arg Glu Leu Tyr Gln Ser Ala Arg Ala Trp Lys Asp His Lys
625                 630                 635                 640

Ala Tyr Ile Asp Lys Glu Ile Glu Ala Leu Gln Asp Lys Ile Lys Asn
                645                 650                 655

Leu Arg Glu Val Arg Gly His Leu Lys Arg Arg Lys Pro Asp Glu Cys
                660                 665                 670

Asp Cys Thr Lys Gln Ser Tyr Tyr Asn Lys Glu Lys Gly Val Lys Thr
                675                 680                 685

Gln Glu Lys Ile Lys Ser His Leu His Pro Phe Lys Glu Ala Ala Gln
                690                 695                 700

Glu Val Asp Ser Lys Leu Gln Leu Phe Lys Glu Asn Arg Arg Arg Lys
705                 710                 715                 720

Lys Glu Arg Lys Gly Lys Lys Arg Gln Lys Lys Gly Asp Glu Cys Ser
                725                 730                 735

Leu Pro Gly Leu Thr Cys Phe Thr His Asp Asn Asn His Trp Gln Thr
                740                 745                 750

Ala Pro Phe Trp Asn Leu Gly Ser Phe Cys Ala Cys Thr Ser Ser Asn
                755                 760                 765

Asn Asn Thr Tyr Trp Cys Leu Arg Thr Val Asn Asp Thr His Asn Phe
770                 775                 780

Leu Phe Cys Glu Phe Ala Thr Gly Phe Leu Glu Phe Asp Met Asn
785                 790                 795                 800

Thr Asp Pro Tyr Gln Leu Thr Asn Thr Val His Thr Val Glu Arg Gly
                805                 810                 815

Ile Leu Asn Gln Leu His Val Gln Leu Met Glu Leu Arg Ser Cys Gln
                820                 825                 830

Gly Tyr Lys Gln Cys Asn Pro Arg Pro Lys Gly Leu Glu Thr Gly Asn
                835                 840                 845

Lys Asp Gly Gly Ser Tyr Asp Pro His Arg Gly Gln Leu Trp Asp Gly
                850                 855                 860

Trp Glu Gly
865
```

<210> SEQ ID NO 3
<211> LENGTH: 709
<212> TYPE: PRT
<213> ORGANISM: Caenorhabditis elegans

<400> SEQUENCE: 3

Met Ile Ser Asn Leu Arg Ile Ser Asn Tyr Phe Ile Ile Phe Tyr Val
1               5                   10                  15

Leu Phe Leu Ile Ile Pro Ile Lys Val Thr Ser Ile His Phe Val Asp
                20                  25                  30

Ser Gln His Asn Val Ile Leu Ile Leu Thr Asp Asp Gln Asp Ile Glu
            35                  40                  45

Leu Gly Ser Met Asp Phe Met Pro Lys Thr Ser Gln Ile Met Lys Glu
        50                  55                  60

Arg Gly Thr Glu Phe Thr Ser Gly Tyr Val Thr Thr Pro Ile Cys Cys
65                  70                  75                  80

Pro Ser Arg Ser Thr Ile Leu Thr Gly Leu Tyr Val His Asn His His
                85                  90                  95

Val His Thr Asn Asn Gln Asn Cys Thr Gly Val Glu Trp Arg Lys Val
            100                 105                 110

His Glu Lys Lys Ser Ile Gly Val Tyr Leu Gln Glu Ala Gly Tyr Arg
        115                 120                 125

Thr Ala Tyr Leu Gly Lys Tyr Leu Asn Glu Tyr Asp Gly Ser Tyr Ile
    130                 135                 140

Pro Pro Gly Trp Asp Glu Trp His Ala Ile Val Lys Asn Ser Lys Phe
145                 150                 155                 160

Tyr Asn Tyr Thr Met Asn Ser Asn Gly Glu Arg Glu Lys Phe Gly Ser
                165                 170                 175

Glu Tyr Glu Lys Asp Tyr Phe Thr Asp Leu Val Thr Asn Arg Ser Leu
            180                 185                 190

Lys Phe Ile Asp Lys His Ile Lys Ile Arg Ala Trp Gln Pro Phe Ala
        195                 200                 205

Leu Ile Ile Ser Tyr Pro Ala Pro His Gly Pro Glu Asp Pro Ala Pro
    210                 215                 220

Gln Phe Ala His Met Phe Glu Asn Glu Ile Ser His Arg Thr Gly Ser
225                 230                 235                 240

Trp Asn Phe Ala Pro Asn Pro Asp Lys Gln Trp Leu Gln Arg Thr
                245                 250                 255

Gly Lys Met Asn Asp Val His Ile Ser Phe Thr Asp Leu Leu His Arg
            260                 265                 270

Arg Arg Leu Gln Thr Leu Gln Ser Val Asp Glu Gly Ile Glu Arg Leu
        275                 280                 285

Phe Asn Leu Leu Arg Glu Leu Asn Gln Leu Trp Asn Thr Tyr Ala Ile
    290                 295                 300

Tyr Thr Ser Asp His Gly Tyr His Leu Gly Gln Phe Gly Leu Leu Lys
305                 310                 315                 320

Gly Lys Asn Met Pro Tyr Glu Phe Asp Ile Arg Val Pro Phe Phe Met
                325                 330                 335

Arg Gly Pro Gly Ile Pro Arg Asn Val Thr Phe Asn Glu Ile Val Thr
            340                 345                 350

Asn Val Asp Ile Ala Pro Thr Met Leu His Ile Ala Gly Val Pro Lys
        355                 360                 365

Pro Ala Arg Met Asn Gly Arg Ser Leu Leu Glu Leu Val Ala Leu Lys

-continued

```
                    370                 375                 380
Lys Lys Lys Lys Lys His Met Thr Ala Leu Lys Pro Trp Arg Asp Thr
385                 390                 395                 400

Ile Leu Ile Glu Arg Gly Lys Met Pro Lys Leu Lys Lys Ile Arg Asp
                405                 410                 415

Arg Tyr Ile Lys Gln Lys Lys Phe Asn Lys Glu Asn Arg Leu Ser
                420                 425             430

Lys Glu Cys Lys Arg Arg Lys Trp Gln Arg Asp Cys Val His Gly Gln
            435                 440                 445

Leu Trp Lys Cys Tyr Tyr Thr Val Glu Asp Arg Trp Arg Ile Tyr Lys
450                 455                 460

Cys Arg Asp Asn Trp Ser Asp Gln Cys Ser Arg Lys Lys Arg Glu
465                 470                 475                 480

Ile Ser Asn Tyr Asp Asp Asp Ile Asp Glu Phe Leu Thr Tyr Ala
                485                 490                 495

Asp Arg Glu Asn Phe Ser Glu Gly His Glu Trp Tyr Gln Gly Glu Phe
                500                 505                 510

Glu Asp Ser Gly Glu Val Gly Glu Leu Asp Gly His Arg Ser Lys
            515                 520                 525

Arg Gly Ile Leu Ser Lys Cys Ser Cys Ser Arg Asn Val Ser His Pro
530                 535                 540

Ile Lys Leu Leu Glu Gln Lys Met Ser Lys Lys His Tyr Leu Lys Tyr
545                 550                 555                 560

Lys Lys Lys Pro Gln Asn Gly Ser Leu Lys Pro Lys Asp Cys Ser Leu
                565                 570                 575

Pro Gln Met Asn Cys Phe Thr His Thr Ala Ser His Trp Lys Thr Pro
                580                 585                 590

Pro Leu Trp Pro Glu Glu Leu Gly Glu Phe Phe Cys Gln Asn Cys
            595                 600                 605

Asn Asn Asn Thr Tyr Trp Cys Leu Arg Thr Lys Asn Glu Thr His Asn
                610                 615                 620

Phe Leu Tyr Cys Glu Phe Val Thr Glu Phe Ile Ser Phe Tyr Asp Phe
625                 630                 635                 640

Asn Thr Asp Pro Asp Gln Leu Ile Asn Ala Val Tyr Ser Leu Asp Ile
                645                 650                 655

Gly Val Leu Glu Gln Leu Ser Glu Gln Leu Arg Asn Leu Arg Lys Cys
                660                 665                 670

Lys Asn Arg Gln Cys Glu Ile Trp Ser Thr Ser Gln Met Leu Arg Ser
                675                 680                 685

Pro Lys Leu Val Asp Leu Arg Val Asn Glu Lys Ser Phe Leu Thr Tyr
690                 695                 700

Gln Pro Glu Lys Thr
705
```

<210> SEQ ID NO 4
<211> LENGTH: 473
<212> TYPE: DNA
<213> ORGANISM: Drosophila sp.
<220> FEATURE:
<221> NAME/KEY: unsure
<222> LOCATION: (372)..(373)
<223> OTHER INFORMATION: a, c, g or t

<400> SEQUENCE: 4
cacttgcaag ccgggctttg ttatcgcaca aatttatgt aaacaaaaga aaacttcgat    60

```
ctgctccatg atcaccttag cccctctgat cgtcctagtc ctcgcttgcc tgggaaacac    120
ggccagcgag aagttgccca acattctgct gatcctgtcc gacgatcagg atgtggagct    180
gcgcggtatg tttcccatgg agcatacgat cgaaatgctg ggtttcggtg gcgccctgtt    240
ccacaacgcc tacacgccct cgcccatctg ctgtccggcg aggacgagtc tgctgacggg    300
catgtatgcg cacaatcacg gcacccggaa caattccgta agtggtggat gctacggacc    360
gcactggcgc gnntgcctgg agcccgggct ttgccataca tcttgcagca gcacggatac    420
aacaccttct ttggcgggaa gtacttgaat cagtactggg gcgctgggga tgt           473
```

<210> SEQ ID NO 5
<211> LENGTH: 540
<212> TYPE: DNA
<213> ORGANISM: Drosophila sp.

<400> SEQUENCE: 5

```
aggattgatc atgaactcca agtactacaa ctacagcatc aacctgaatg acaaaaaat     60 taagcacggt tttgactacg ctaaagacta ctatccggat ctgatagcca atgactcgat    120
tgccttcctc cgctcctcaa agcaacagaa ccagcggaag cagtgctgct caccatgagt    180
tttcctgcac acatggccc tgaggattcg gctccccagt atagtcatct cttctttaat     240
gtgacaaccc atcacactcc atcgtatgat cacgccccaa atccggacaa gcaatggatc    300
ctgagggtca cggaacccat gcagcctgtt cacaaaaggt tcaccaatct gctcatgacg    360
aagcgactgc aaacgctcca aagtgtcgac gttgccgtgg agcgggttta taacgagcta    420
aaagaactcg gagagctgga caacacttat atagtataca cttccgatca tggttatcat    480
ctgggtcagt ttggacttat taaggaaaa agttttccct ttgagtttga tgatcgtgtg     540
```

<210> SEQ ID NO 6
<211> LENGTH: 482
<212> TYPE: DNA
<213> ORGANISM: Mus sp.

<400> SEQUENCE: 6

```
aattcggacc ttgggaagtg aggggacacc taaagaaaag gaaacctgag gagtgtggct     60
gtggtgacca gagctattac aacaaagaga aggtgtcaa acgacaggag aagctaaaga    120
gtcaccttca ccccttcaag gaggctgctg cccaggaggt ggatagcaaa cttcagctct    180
tcaaggagca tcggaggagg aagaaggaga ggaaggagaa gaaacggcag aggaagggag    240
aggagtgtag cctgcctggc cttacctgct tcacccatga caacaaccac tggcagactg    300
ccccattctg gaacttggga tcttttctgtg cctgcacaag ttctaacaac aatacctact    360
gggtgttgcg tacagtcaac gagacgcaca atttcctgtt ttgtgagttt gctactggct    420
ttctggaata tttcgacatg aatacggatc cttatcagct cacaaataca gtacacacag    480
ta                                                                    482
```

<210> SEQ ID NO 7
<211> LENGTH: 160
<212> TYPE: PRT
<213> ORGANISM: Mus sp.

<400> SEQUENCE: 7

Phe Gly Pro Trp Glu Val Arg Gly His Leu Lys Lys Arg Lys Pro Glu
 1               5                  10                  15

Glu Cys Gly Cys Gly Asp Gln Ser Tyr Tyr Asn Lys Glu Lys Gly Val
            20                  25                  30

```
Lys Arg Gln Glu Lys Leu Lys Ser His Leu His Pro Phe Lys Glu Ala
            35                  40                  45

Ala Ala Gln Glu Val Asp Ser Lys Leu Gln Leu Phe Lys Glu His Arg
    50                  55                  60

Arg Arg Lys Lys Glu Arg Lys Glu Lys Lys Arg Gln Arg Lys Gly Glu
65              70                  75                  80

Glu Cys Ser Leu Pro Gly Leu Thr Cys Phe Thr His Asp Asn Asn His
                85                  90                  95

Trp Gln Thr Ala Pro Phe Trp Asn Leu Gly Ser Phe Cys Ala Cys Thr
            100                 105                 110

Ser Ser Asn Asn Asn Thr Tyr Trp Val Leu Arg Thr Val Asn Glu Thr
        115                 120                 125

His Asn Phe Leu Phe Cys Glu Phe Ala Thr Gly Phe Leu Glu Tyr Phe
    130                 135                 140

Asp Met Asn Thr Asp Pro Tyr Gln Leu Thr Asn Thr Val His Thr Val
145                 150                 155                 160

<210> SEQ ID NO 8
<211> LENGTH: 538
<212> TYPE: DNA
<213> ORGANISM: Mus sp.

<400> SEQUENCE: 8
gtagcaccga tgggtcactt tgatgggatt gggggcagaa taatctggaa ggccaccagt      60
accactgaaa ctgccaccat ccttgtcatc ttggtcttca gggcccctg agcagtgcgg      120
cttgctaagg ttgcggggct gaggcacagt atccaagcct acgtggtata tctcaccgtc     180
cacctcgatg gccacggaac ggatggagcg gttccgggca tagctggtct tatactttt      240
cttaaagagc ttacggcgtc cagccaggcc cagtttgtag tcccctccac cgccactgtc    300
acagctgcag gcctcgctgc tctggccgtc atacttgggc accaggttgg agagggctct    360
gctgccaccg ccgccaccaa accgcatggg gcctttacat tgtgcagct cagcgtccc      420
agaagcgtcc tccacacact gccacttctg ccccagctgt tcgcatgctg tctggtactc    480
agctcgctga cacaggtcct tcacgcgctg gtacttgggc aggaagttct cctcctgg      538

<210> SEQ ID NO 9
<211> LENGTH: 466
<212> TYPE: DNA
<213> ORGANISM: Mus sp.

<400> SEQUENCE: 9
cgacttggac ctgtacaagt ccctgcaggc ttggaaagac cacaagctgc acatcgacca      60
tgagatcgaa accctgcaga caaaattaa gaaccttcga gaagtcaggg gtcacctgaa     120
gaagaagcga ccggaagaat gtgactgcca taaatcagt taccacagcc aacacaaagg     180
ccgtctcaag cacaaaggct ccagcctgca ccctttcagg aagggtctgc aggagaagga    240
caaggtgtgg ctgctgcggg acagaaacgc aagaagaaac tgcgcaactg ctcaaacggc    300
tgcagaacaa cgatacgtgc agcatgcccg gcctcacgtg ctttacccac gacaaccacc    360
actggcagac ggcgccactc tggacgctgg ggccgttctg cgcctgcacc agcgccaaca    420
acaacacgta ctggtgcttg aggaccataa atgagaccca caactt                   466

<210> SEQ ID NO 10
<211> LENGTH: 494
<212> TYPE: DNA
```

-continued

<213> ORGANISM: Mus sp.

<400> SEQUENCE: 10

```
agaagaagcg accggaagaa tgtgactgcc ataaaatcag ttaccacagc caacacaaag      60
gccgtctcaa gcacaaaggc tccagcctgc acccttcag gaagggtctg caggagaagg     120
acaaggtgtg gctgctgcgg gacagaaacg caagaagaaa ctgcgcaact gctcaaacgg    180
ctgcagaaca acgatacgtg cagcatgccg gcctcacgtg ctttaccac gacaaccacc     240
actggcagac ggcgccactc tggacgctgg ggccgttctg cgcctgcacc agcgccaaca    300
acaacacgta ctggtgcttg aggaccataa atgagaccca caacttcctc ttctgcgaat    360
ttgcaaccgg cttcatagaa tactttgacc tcagtacaga cccctaccag ctgatgaacg    420
cggtgaacac actggacagg gacgtcctta accaactgca cgtgcagctc atggagctaa    480
ggagctgtaa aggg                                                      494
```

<210> SEQ ID NO 11
<211> LENGTH: 436
<212> TYPE: DNA
<213> ORGANISM: Mus sp.

<400> SEQUENCE: 11

```
agcagagccc tctccaacct ggtgcccaag tatgacggcc agagcagcga ggcctgcagc     60
tgtgacagtg gcggtggagg ggactacaaa ctgggcctgg ctggacgccg taagctcttt    120
aagaaaaagt ataagaccag ctatgcccgg aaccgctcca tccgttccgt ggccatcgag    180
gtggacggtg agatatacca cgtaggcttg gatactgtgc ctcagccccg caaccttagc    240
aagccgcact ggccagggc ccgtgaagac caagatgaca aggatggtgg cagtttcagt    300
ggtactggtg gccttccaga ttattctgcc cccaatccca tcaaagtgac ccatcggtgc    360
tacatccttg agaatgacac agtccagtgc gacttggacc tgtacaagtc cctgcaggct    420
tggaaagacc acaagc                                                    436
```

<210> SEQ ID NO 12
<211> LENGTH: 459
<212> TYPE: DNA
<213> ORGANISM: Mus sp.

<400> SEQUENCE: 12

```
cccacgacaa ccaccactgg cagacggcgc cactctggac gctggggccg ttctgcgcct     60
gcaccagcgc caacaacaac acgtactggt gcttgaggac cataaatgag acccacaact    120
tcctcttctg cgaatttgca accggcttca tagaatactt tgacctcagt acagaccct    180
accagctgat gaacgcggtg aacacactgg acagggacgt ccttaaccaa ctgcacgtgc    240
agctcatgga gctaaggagc tgtaaaggct acaagcagtg caacccccgg acccgcaaca    300
tggacctggg gcttagagac ggaggaagct atgaacaata caggcagttt cagcgtcgaa    360
aatggccaga aatgaagaga ccttcttcca atcactggg acagctatgg aaggttggg     420
aaggctaagc ggccatagag agaggaactc caaaaccag                           459
```

<210> SEQ ID NO 13
<211> LENGTH: 1367
<212> TYPE: DNA
<213> ORGANISM: Mus sp.

<400> SEQUENCE: 13

```
ccaggaggag aacttcctgc ccaagtacca gcgcgtgaag gacctgtgtc agcgagctga     60
```

-continued

```
gtaccagaca gcatgcgaac agctggggca gaagtggcag tgtgtggagg acgcttctgg        120
gacgctgaag ctgcacaaat gtaaaggccc catgcggttt ggtggcggcg gtggcagcag        180
agccctctcc aacctggtgc ccaagtatga cggccagagc agcgaggcct gcagctgtga        240
cagtggcggt ggagggggact acaaactggg cctggctgga cgccgtaagc tctttaagaa       300
aaagtataag accagctatg cccggaaccg ctccatccgt tccgtggcca tcgaggtgga        360
cggtgagata taccacgtag gcttggatac tgtgcctcag ccccgcaacc ttagcaagcc        420
gcactgsyca ggggcccstg aagaccaaga tgacaaggat ggtggcagtt tcagtggtac        480
tggtggcctt ccagattatt ctgcccccaa tcccatcaaa gtgacccatc ggtgctacat        540
ccttgagaat gacacagtcc agtgcgactt ggacctgtac aagtccctgc aggcttggaa        600
agaccacaag ctgcacatcg accatgagat cgaaaccctg cagaacaaaa ttaagaacct        660
tcgagaagtc agggtcacc tgaagaagaa gcgaccggaa gaatgtgact gccataaaat         720
cagttaccac agccaacaca aaggccgtct caagcacaaa ggctccagcc tgcacccttt        780
caggaagggt ctgcaggaga aggacaaggt gtggctgctg cgggacagaa acgcaagaag        840
aaactgcgca actgctcaaa cggctgcaga acaacgatac gtgcagcatg ccggcctcac        900
gtgctttacc cacgacaacc accactggca gacggcgcca ctctggacgc tggggccgtt        960
ctgcgcctgc accagcgcca acaacaacac gtactggtgc ttgaggacca taatgagac        1020 ccacaacttc ctcttctgcg aatttgcaac cggcttcata gaatactttg acctcagtac       1080
agacccctac cagctgatga acgcggtgaa cacactggca agggacgtcc ttaaccaact       1140
gcacgtgcag ctcatggagc taaggagctg taaaggctac aagcagtgca acccccggac       1200
ccgcaacatg gacctgggc ttagagacgg aggaagctat gaacaataca ggcagtttca        1260
gcgtcgaaaa tggccagaaa tgaagagacc ttcttccaaa tcactgggac agctatggga       1320
aggttgggaa ggctaagcgg ccatagagag aggaactcca aaaccag                      1367
```

<210> SEQ ID NO 14
<211> LENGTH: 455
<212> TYPE: PRT
<213> ORGANISM: Mus sp.
<220> FEATURE:
<221> NAME/KEY: UNSURE
<222> LOCATION: (142-143)
<223> OTHER INFORMATION: any amino acid
<220> FEATURE:
<221> NAME/KEY: UNSURE
<222> LOCATION: (146)
<223> OTHER INFORMATION: any amino acid
<220> FEATURE:
<221> NAME/KEY: UNSURE
<222> LOCATION: (445)
<223> OTHER INFORMATION: any amino acid

<400> SEQUENCE: 14

```
Gln Glu Glu Asn Phe Leu Pro Lys Tyr Gln Arg Val Lys Asp Leu Cys
  1               5                  10                  15

Gln Arg Ala Glu Tyr Gln Thr Ala Cys Glu Gln Leu Gly Gln Lys Trp
             20                  25                  30

Gln Cys Val Glu Asp Ala Ser Gly Thr Leu Lys Leu His Lys Cys Lys
         35                  40                  45

Gly Pro Met Arg Phe Gly Gly Gly Gly Ser Arg Ala Leu Ser Asn
     50                  55                  60

Leu Val Pro Lys Tyr Asp Gly Gln Ser Ser Glu Ala Cys Ser Cys Asp
 65                  70                  75                  80
```

```
Ser Gly Gly Gly Gly Asp Tyr Lys Leu Gly Leu Ala Gly Arg Arg Lys
                85                  90                  95

Leu Phe Lys Lys Lys Tyr Lys Thr Ser Tyr Ala Arg Asn Arg Ser Ile
            100                 105                 110

Arg Ser Val Ala Ile Glu Val Asp Gly Glu Ile Tyr His Val Gly Leu
            115                 120                 125

Asp Thr Val Pro Gln Pro Arg Asn Leu Ser Lys Pro His Xaa Xaa Gly
130                 135                 140

Ala Xaa Glu Asp Gln Asp Asp Lys Asp Gly Gly Ser Phe Ser Gly Thr
145                 150                 155                 160

Gly Gly Leu Pro Asp Tyr Ser Ala Pro Asn Pro Ile Lys Val Thr His
            165                 170                 175

Arg Cys Tyr Ile Leu Glu Asn Asp Thr Val Gln Cys Asp Leu Asp Leu
            180                 185                 190

Tyr Lys Ser Leu Gln Ala Trp Lys Asp His Lys Leu His Ile Asp His
            195                 200                 205

Glu Ile Glu Thr Leu Gln Asn Lys Ile Lys Asn Leu Arg Glu Val Arg
210                 215                 220

Gly His Leu Lys Lys Lys Arg Pro Glu Glu Cys Asp Cys His Lys Ile
225                 230                 235                 240

Ser Tyr His Ser Gln His Lys Gly Arg Leu Lys His Lys Gly Ser Ser
            245                 250                 255

Leu His Pro Phe Arg Lys Gly Leu Gln Glu Lys Asp Lys Val Trp Leu
            260                 265                 270

Leu Arg Asp Arg Asn Ala Arg Arg Asn Cys Ala Thr Ala Gln Thr Ala
            275                 280                 285

Ala Glu Gln Arg Tyr Val Gln His Ala Gly Leu Thr Cys Phe Thr His
290                 295                 300

Asp Asn His His Trp Gln Thr Ala Pro Leu Trp Thr Leu Gly Pro Phe
305                 310                 315                 320

Cys Ala Cys Thr Ser Ala Asn Asn Asn Thr Tyr Trp Cys Leu Arg Thr
            325                 330                 335

Ile Asn Glu Thr His Asn Phe Leu Phe Cys Glu Phe Ala Thr Gly Phe
            340                 345                 350

Ile Glu Tyr Phe Asp Leu Ser Thr Asp Pro Tyr Gln Leu Met Asn Ala
            355                 360                 365

Val Asn Thr Leu Asp Arg Asp Val Leu Asn Gln Leu His Val Gln Leu
370                 375                 380

Met Glu Leu Arg Ser Cys Lys Gly Tyr Lys Gln Cys Asn Pro Arg Thr
385                 390                 395                 400

Arg Asn Met Asp Leu Gly Leu Arg Asp Gly Ser Tyr Glu Gln Tyr
            405                 410                 415

Arg Gln Phe Gln Arg Arg Lys Trp Pro Glu Met Lys Arg Pro Ser Ser
            420                 425                 430

Lys Ser Leu Gly Gln Leu Trp Glu Gly Trp Glu Gly Xaa Ala Ala Ile
            435                 440                 445

Glu Arg Gly Thr Pro Lys Pro
450                 455

<210> SEQ ID NO 15
<211> LENGTH: 4834
<212> TYPE: DNA
<213> ORGANISM: Homo sapiens
```

-continued

<400> SEQUENCE: 15

```
gatgtggagc tggggtccct gcaagtcatg aacaaaacga gaaagattat ggaacatggg      60
ggggccacct tcatcaatgc ctttgtgact acacccatgt gctgcccgtc acggtcctcc     120
atgctcaccg ggaagtatgt gcacaatcac aatgtctaca ccaacaacga gaactgctct     180
tcccctcgt ggcaggccat gcatgagcct cggacttttg ctgtatatct taacaacact     240
ggctacagaa cagccttttt tggaaaatac ctcaatgaat ataatggcag ctacatcccc     300
cctgggtggc gagaatggct tggattaatc aagaattctc gcttctataa ttacactgtt     360
tgtcgcaatg gcatcaaaga aaagcatgga tttgattatg caaaggacta cttcacagac     420
ttaatcacta cgagagcat taattacttc aaaatgtcta agagaatgta tccccatagg      480
cccgttatga tggtgatcag ccacgctgcg ccccacggcc ccgaggactc agccccacag     540
ttttctaaac tgtaccccaa tgcttcccaa cataactc ctagttataa ctatgcacca      600
aatatggata aacactggat tatgcagtac acaggaccaa tgctgcccat ccacatggaa     660
tttacaaaca ttctacagcg caaaaggctc cagactttga tgtcagtgga tgattctgtg     720
gagaggctgt ataacatgct cgtggagacg ggggagctgg agaatactta catcatttac     780
accgccgacc atggttacca tattgggcag tttggactgg tcaaggggaa atccatgcca     840
tatgactttg atattcgtgt gcctttttt attcgtggtc caagtgtaga accaggatca     900
atagtcccac agatcgttct caacattgac ttggccccca cgatcctgga tattgctggg     960
ctcgacacac tcctgatgt ggacggcaag tctgtcctca aacttctgga cccagaaaag    1020
ccaggtaaca ggtttcgaac aaacaagaag gccaaaattt ggcgtgatac attcctagtg    1080
gaaagaggca aatttctacg taagaaggaa gaatccagca agaatatcca acagtcaaat    1140
cacttgccca aatatgaacg ggtcaaagaa ctatgccagc aggccaggta ccagacagcc    1200
tgtgaacaac cggggcagaa gtggcaatgc attgaggata catctggcaa gcttcgaatt    1260
cacaagtgta aaggacccag tgacctgctc acagtccggc agagcacgcg gaacctctac    1320
gctcgcggct ccatgacaa agacaaagag tgcagttgta gggagtctgg ttaccgtgcc    1380
agcagaagcc aaagaaagag tcaacggcaa ttcttgagaa accaggggac tccaaagtac    1440
aagcccagat ttgtccatac tcggcagaca cgttccttgt ccgtcgaatt tgaaggtgaa    1500
atatatgaca taaatctgga agaagaagaa gaattgcaag tgttgcaacc aagaaacatt    1560
gctaagcgtc atgatgaagg ccacaagggg ccaagagatc tccaggcttc cagtggtggc    1620
aacagggca ggatgctggc agatagcagc aacgccgtgg gcccacctac cactgtccga     1680
gtgacacaca gtgtttttat tcttcccaat gactctatcc attgtgagag gaactgtac    1740
caatcggcca gagcgtggaa ggaccataag gcatacattg acaaagagat tgaagctctg    1800
caagataaaa ttaagaattt aagagaagtg agaggacatc tgaagagaag gaagcctgag    1860
gaatgtagct gcagtaaaca aagctattac aataaagaga aggtgtaaa aaagcaagag     1920
aaattaaaga gccatcttca cccattcaag gaggctgctc aggaagtaga tagcaaactg    1980
caactttca aggagaacaa ccgtaggagg aagaaggaga ggaaggagaa gagacggcag    2040
aggaaggggg aagagtgcag cctgcctggc ctcacttgct tcacgcatga caacaaccac    2100
tggcagacag ccccgttctg gaacctggga tctttctgtg cttgcacgag ttctaacaat    2160
aacacctact ggtgtttgcg tacagttaat gagacgcata atttttcttt ctgtgagttt    2220
gctactggcc ttttggagta ttttgatatg aatacagatc cttatcagct cacaaataca    2280
gtgcacacgg tagaacgagg cattttgaat cagctacacg tacaactaat ggagctcaga    2340
```

```
agctgtcaag gatataagca gtgcaaccca agacctaaga atcttgatgt tggaaataaa    2400
gatggaggaa gctatgacct acacagagga cagttatggg atggatggga aggttaatca    2460
gccccgtctc actgcagaca tcaactggca aggcctagag gagctacaca gtgtgaatga    2520
aaacatctat gagtacagac aaaactacag acttagtctg gtggactgga ctaattactt    2580
gaaggattta gatagagtat ttgcactgct gaagagtcac tatgagcaaa ataaaacaaa    2640
taagactcaa actgctcaaa gtgacggstt cttggttgtc tctgctgagc acgctgtgtc    2700
aatggagatg gcctctgctg actcagatga agacccaagg cataaggttg ggaaaacacc    2760
tcatttgacc ttgccagctg accttcaaac cctgcatttg aaccgaccaa cattaagtcc    2820
agagagtaaa cttgaatgga ataacgacat tccagaagtt aatcatttga attctgaaca    2880
ctggagaaaa accgaaaaat ggacggggca tgaagagact aatcatctgg aaaccgattt    2940
cagtggcgat ggcatgacag agctagagct cgggcccagc cccaggctgc agcccattcg    3000
caggcacccg aaagaacttc cccagtatgg tggtcctgga aaggacattt ttgaagatca    3060
actatatctt cctgtgcatt ccgatggaat ttcagttcat cagatgttca ccatggccac    3120
cgcagaacac cgaagtaatt ccagcatagc ggggaagatg ttgaccaagg tggagaagaa    3180
tcacgaaaag gagaagtcac agcacctaga aggcagcgcc tcctcttcac tctcctctga    3240
ttagatgaaa ctgttacctt accctaaaca cagtatttct ttttaacttt tttatttgta    3300
aactaataaa ggtaatcaca gccaccaaca ttccaagcta ccctgggtac ctttgtgcag    3360
tagaagctag tgagcatgtg agcaagcggt gtgcacacgg agactcatcg ttataattta    3420
ctatctgcca agagtagaaa gaaaggctgg ggatatttgg gttggcttgg ttttgatttt    3480
ttgcttgttt gtttgttttg tactaaaaca gtattatctt ttgaatatcg tagggacata    3540
agtatataca tgttatccaa tcaagatggc tagaatggtg cctttctgag tgtctaaaac    3600
ttgacacccc tggtaaatct ttcaacacac ttccactgcc tgcgtaatga agttttgatt    3660
catttttaac cactggaatt tttcaatgcc gtcatttca gttagatgat tttgcactttt    3720 gagattaaaa tgccatgtct atttgattag tcttattttt ttatttttac aggcttatca    3780
gtctcactgt tggctgtcat tgtgacaaag tcaaataaac ccccaaggac gacacacagt    3840
atggatcaca tattgtttga cattaagctt ttgccagaaa atgttgcatg tgttttacct    3900
cgacttgcta aaatcgatta gcagaaaggc atggctaata atgttggtgg tgaaaataaa    3960
taaataagta aacaaaatga agattgcctg ctctctctgt gcctagcctc aaagcgttca    4020
tcatacatca tacctttaag attgctatat tttgggttat tttcttgaca ggagaaaaag    4080
atctaaagat cttttatttt catctttttt ggttttcttg gcatgactaa gaagcttaaa    4140
tgttgataaa atatgactag ttttgaattt acaccaagaa cttctcaata aagaaaatc    4200 atgaatgctc cacaatttca acataccaca agagaagtta atttcttaac attgtgttct    4260
atgattattt gtaagacctt caccaagttc tgatatcttt taaagacata gttcaaaatt    4320
gcttttgaaa atctgtattc ttgaaaatat ccttgttgtg tattaggttt ttaaatacca    4380
gctaaaggat tacctcactg agtcatcagt accctcctat tcagctcccc aagatgatgt    4440 gttttttgctt accctaagag aggttttctt cttattttta gataattcaa gtgcttagat    4500
aaattatgtt ttctttaagt gtttatggta aactctttta aagaaaattt aatatgttat    4560
agctgaatct ttttggtaac tttaaatctt tatcatagac tctgtacata tgttcaaatt    4620
agctgcttgc ctgatgtgtg tatcatcggt gggatgacag aacaaacata tttatgatca    4680
```

```
tgaataatgt gctttgtaaa aagatttcaa gttattagga agcatactct gttttttaat    4740
catgtataat attccatgat actttttatag aacaattctg gcttcaggaa agtctagaag   4800
caatatttct tcaaataaaa ggtgtttaaa cttt                                4834
```

<210> SEQ ID NO 16
<211> LENGTH: 1611
<212> TYPE: PRT
<213> ORGANISM: Homo sapiens
<220> FEATURE:
<221> NAME/KEY: UNSURE
<222> LOCATION: (819)
<223> OTHER INFORMATION: any amino acid
<220> FEATURE:
<221> NAME/KEY: UNSURE
<222> LOCATION: (840)
<223> OTHER INFORMATION: any amino acid
<220> FEATURE:
<221> NAME/KEY: UNSURE
<222> LOCATION: (844)
<223> OTHER INFORMATION: any amino acid
<220> FEATURE:
<221> NAME/KEY: UNSURE
<222> LOCATION: (852)
<223> OTHER INFORMATION: any amino acid
<220> FEATURE:
<221> NAME/KEY: UNSURE
<222> LOCATION: (858)
<223> OTHER INFORMATION: any amino acid
<220> FEATURE:
<221> NAME/KEY: UNSURE
<222> LOCATION: (865)
<223> OTHER INFORMATION: any amino acid
<220> FEATURE:
<221> NAME/KEY: UNSURE
<222> LOCATION: (875)
<223> OTHER INFORMATION: any amino acid
<220> FEATURE:
<221> NAME/KEY: UNSURE
<222> LOCATION: (878)
<223> OTHER INFORMATION: any amino acid
<220> FEATURE:
<221> NAME/KEY: UNSURE
<222> LOCATION: (881)
<223> OTHER INFORMATION: any amino acid
<220> FEATURE:
<221> NAME/KEY: UNSURE
<222> LOCATION: (888)
<223> OTHER INFORMATION: any amino acid
<220> FEATURE:
<221> NAME/KEY: UNSURE
<222> LOCATION: (896)
<223> OTHER INFORMATION: any amino acid
<220> FEATURE:
<221> NAME/KEY: UNSURE
<222> LOCATION: (907)
<223> OTHER INFORMATION: any amino acid
<220> FEATURE:
<221> NAME/KEY: UNSURE
<222> LOCATION: (910)
<223> OTHER INFORMATION: any amino acid
<220> FEATURE:
<221> NAME/KEY: UNSURE
<222> LOCATION: (915)
<223> OTHER INFORMATION: any amino acid
<220> FEATURE:
<221> NAME/KEY: UNSURE
<222> LOCATION: (927)
<223> OTHER INFORMATION: any amino acid
<220> FEATURE:
<221> NAME/KEY: UNSURE
<222> LOCATION: (943)
<223> OTHER INFORMATION: any amino acid
<220> FEATURE:
<221> NAME/KEY: UNSURE
<222> LOCATION: (945)
<223> OTHER INFORMATION: any amino acid -continued

```
<220> FEATURE:
<221> NAME/KEY: UNSURE
<222> LOCATION: (948)
<223> OTHER INFORMATION: any amino acid
<220> FEATURE:
<221> NAME/KEY: UNSURE
<222> LOCATION: (954)
<223> OTHER INFORMATION: any amino acid
<220> FEATURE:
<221> NAME/KEY: UNSURE
<222> LOCATION: (959)
<223> OTHER INFORMATION: any amino acid
<220> FEATURE:
<221> NAME/KEY: UNSURE
<222> LOCATION: (971)
<223> OTHER INFORMATION: any amino acid
<220> FEATURE:
<221> NAME/KEY: UNSURE
<222> LOCATION: (974)
<223> OTHER INFORMATION: any amino acid
<220> FEATURE:
<221> NAME/KEY: UNSURE
<222> LOCATION: (1018)
<223> OTHER INFORMATION: any amino acid
<220> FEATURE:
<221> NAME/KEY: UNSURE
<222> LOCATION: (1046)
<223> OTHER INFORMATION: any amino acid
<220> FEATURE:
<221> NAME/KEY: UNSURE
<222> LOCATION: (1080)
<223> OTHER INFORMATION: any amino acid
<220> FEATURE:
<221> NAME/KEY: UNSURE
<222> LOCATION: (1089)
<223> OTHER INFORMATION: any amino acid
<220> FEATURE:
<221> NAME/KEY: UNSURE
<222> LOCATION: (1102)..(1103)
<223> OTHER INFORMATION: any amino acid
<220> FEATURE:
<221> NAME/KEY: UNSURE
<222> LOCATION: (1105)
<223> OTHER INFORMATION: any amino acid
<220> FEATURE:
<221> NAME/KEY: UNSURE
<222> LOCATION: (1121)
<223> OTHER INFORMATION: any amino acid
<220> FEATURE:
<221> NAME/KEY: UNSURE
<222> LOCATION: (1127)
<223> OTHER INFORMATION: any amino acid
<220> FEATURE:
<221> NAME/KEY: UNSURE
<222> LOCATION: (1191)
<223> OTHER INFORMATION: any amino acid
<220> FEATURE:
<221> NAME/KEY: UNSURE
<222> LOCATION: (1199)
<223> OTHER INFORMATION: any amino acid
<220> FEATURE:
<221> NAME/KEY: UNSURE
<222> LOCATION: (1223)
<223> OTHER INFORMATION: any amino acid
<220> FEATURE:
<221> NAME/KEY: UNSURE
<222> LOCATION: (1235)
<223> OTHER INFORMATION: any amino acid
<220> FEATURE:
<221> NAME/KEY: UNSURE
<222> LOCATION: (1250)
<223> OTHER INFORMATION: any amino acid
<220> FEATURE:
<221> NAME/KEY: UNSURE
<222> LOCATION: (1307)
<223> OTHER INFORMATION: any amino acid
<220> FEATURE:
<221> NAME/KEY: UNSURE
<222> LOCATION: (1321)
```

```
<223> OTHER INFORMATION: any amino acid
<220> FEATURE:
<221> NAME/KEY: UNSURE
<222> LOCATION: (1356)
<223> OTHER INFORMATION: any amino acid
<220> FEATURE:
<221> NAME/KEY: UNSURE
<222> LOCATION: (1362)
<223> OTHER INFORMATION: any amino acid
<220> FEATURE:
<221> NAME/KEY: UNSURE
<222> LOCATION: (1382)..(1383)
<223> OTHER INFORMATION: any amino acid
<220> FEATURE:
<221> NAME/KEY: UNSURE
<222> LOCATION: (1397)
<223> OTHER INFORMATION: any amino acid
<220> FEATURE:
<221> NAME/KEY: UNSURE
<222> LOCATION: (1431)
<223> OTHER INFORMATION: any amino acid
<220> FEATURE:
<221> NAME/KEY: UNSURE
<222> LOCATION: (1437)
<223> OTHER INFORMATION: any amino acid
<220> FEATURE:
<221> NAME/KEY: UNSURE
<222> LOCATION: (1448)
<223> OTHER INFORMATION: any amino acid
<220> FEATURE:
<221> NAME/KEY: UNSURE
<222> LOCATION: (1458)
<223> OTHER INFORMATION: any amino acid
<220> FEATURE:
<221> NAME/KEY: UNSURE
<222> LOCATION: (1467)
<223> OTHER INFORMATION: any amino acid
<220> FEATURE:
<221> NAME/KEY: UNSURE
<222> LOCATION: (1479)
<223> OTHER INFORMATION: any amino acid
<220> FEATURE:
<221> NAME/KEY: UNSURE
<222> LOCATION: (1495)
<223> OTHER INFORMATION: any amino acid
<220> FEATURE:
<221> NAME/KEY: UNSURE
<222> LOCATION: (1506)
<223> OTHER INFORMATION: any amino acid
<220> FEATURE:
<221> NAME/KEY: UNSURE
<222> LOCATION: (1522)
<223> OTHER INFORMATION: any amino acid
<220> FEATURE:
<221> NAME/KEY: UNSURE
<222> LOCATION: (1559)
<223> OTHER INFORMATION: any amino acid
<220> FEATURE:
<221> NAME/KEY: UNSURE
<222> LOCATION: (1561)
<223> OTHER INFORMATION: any amino acid
<220> FEATURE:
<221> NAME/KEY: UNSURE
<222> LOCATION: (1583)
<223> OTHER INFORMATION: any amino acid
<220> FEATURE:
<221> NAME/KEY: UNSURE
<222> LOCATION: (1590)
<223> OTHER INFORMATION: any amino acid
<220> FEATURE:
<221> NAME/KEY: UNSURE
<222> LOCATION: (1599)
<223> OTHER INFORMATION: any amino acid
<220> FEATURE:
<221> NAME/KEY: UNSURE
<222> LOCATION: (1606)
<223> OTHER INFORMATION: any amino acid

<400> SEQUENCE: 16
```

-continued

```
Asp Val Glu Leu Gly Ser Leu Gln Val Met Asn Lys Thr Arg Lys Ile
 1               5                  10                  15

Met Glu His Gly Gly Ala Thr Phe Ile Asn Ala Phe Val Thr Thr Pro
             20                  25                  30

Met Cys Cys Pro Ser Arg Ser Ser Met Leu Thr Gly Lys Tyr Val His
         35                  40                  45

Asn His Asn Val Tyr Thr Asn Asn Glu Asn Cys Ser Ser Pro Ser Trp
     50                  55                  60

Gln Ala Met His Glu Pro Arg Thr Phe Ala Val Tyr Leu Asn Asn Thr
 65                  70                  75                  80

Gly Tyr Arg Thr Ala Phe Phe Gly Lys Tyr Leu Asn Glu Tyr Asn Gly
                 85                  90                  95

Ser Tyr Ile Pro Pro Gly Trp Arg Glu Trp Leu Gly Leu Ile Lys Asn
             100                 105                 110

Ser Arg Phe Tyr Asn Tyr Thr Val Cys Arg Asn Gly Ile Lys Glu Lys
         115                 120                 125

His Gly Phe Asp Tyr Ala Lys Asp Tyr Phe Thr Asp Leu Ile Thr Asn
130                 135                 140

Glu Ser Ile Asn Tyr Phe Lys Met Ser Lys Arg Met Tyr Pro His Arg
145                 150                 155                 160

Pro Val Met Met Val Ile Ser His Ala Ala Pro His Gly Pro Glu Asp
                 165                 170                 175

Ser Ala Pro Gln Phe Ser Lys Leu Tyr Pro Asn Ala Ser Gln His Ile
             180                 185                 190

Thr Pro Ser Tyr Asn Tyr Ala Pro Asn Met Asp Lys His Trp Ile Met
         195                 200                 205

Gln Tyr Thr Gly Pro Met Leu Pro Ile His Met Glu Phe Thr Asn Ile
210                 215                 220

Leu Gln Arg Lys Arg Leu Gln Thr Leu Met Ser Val Asp Asp Ser Val
225                 230                 235                 240

Glu Arg Leu Tyr Asn Met Leu Val Glu Thr Gly Glu Leu Glu Asn Thr
                 245                 250                 255

Tyr Ile Ile Tyr Thr Ala Asp His Gly Tyr His Ile Gly Gln Phe Gly
             260                 265                 270

Leu Val Lys Gly Lys Ser Met Pro Tyr Asp Phe Asp Ile Arg Val Pro
         275                 280                 285

Phe Phe Ile Arg Gly Pro Ser Val Glu Pro Gly Ser Ile Val Pro Gln
290                 295                 300

Ile Val Leu Asn Ile Asp Leu Ala Pro Thr Ile Leu Asp Ile Ala Gly
305                 310                 315                 320

Leu Asp Thr Pro Pro Asp Val Asp Gly Lys Ser Val Leu Lys Leu Leu
                 325                 330                 335

Asp Pro Glu Lys Pro Gly Asn Arg Phe Arg Thr Asn Lys Lys Ala Lys
             340                 345                 350

Ile Trp Arg Asp Thr Phe Leu Val Glu Arg Gly Lys Phe Leu Arg Lys
         355                 360                 365

Lys Glu Glu Ser Ser Lys Asn Ile Gln Gln Ser Asn His Leu Pro Lys
370                 375                 380

Tyr Glu Arg Val Lys Glu Leu Cys Gln Gln Ala Arg Tyr Gln Thr Ala
385                 390                 395                 400

Cys Glu Gln Pro Gly Gln Lys Trp Gln Cys Ile Glu Asp Thr Ser Gly
                 405                 410                 415
```

-continued

```
Lys Leu Arg Ile His Lys Cys Lys Gly Pro Ser Asp Leu Leu Thr Val
            420                 425                 430

Arg Gln Ser Thr Arg Asn Leu Tyr Ala Arg Gly Phe His Asp Lys Asp
            435                 440                 445

Lys Glu Cys Ser Cys Arg Glu Ser Gly Tyr Arg Ala Ser Arg Ser Gln
450                 455                 460

Arg Lys Ser Gln Arg Gln Phe Leu Arg Asn Gln Gly Thr Pro Lys Tyr
465                 470                 475                 480

Lys Pro Arg Phe Val His Thr Arg Gln Thr Arg Ser Leu Ser Val Glu
                485                 490                 495

Phe Glu Gly Glu Ile Tyr Asp Ile Asn Leu Glu Glu Glu Glu Glu Leu
            500                 505                 510

Gln Val Leu Gln Pro Arg Asn Ile Ala Lys Arg His Asp Glu Gly His
            515                 520                 525

Lys Gly Pro Arg Asp Leu Gln Ala Ser Ser Gly Gly Asn Arg Gly Arg
530                 535                 540

Met Leu Ala Asp Ser Ser Asn Ala Val Gly Pro Pro Thr Thr Val Arg
545                 550                 555                 560

Val Thr His Lys Cys Phe Ile Leu Pro Asn Asp Ser Ile His Cys Glu
                565                 570                 575

Arg Glu Leu Tyr Gln Ser Ala Arg Ala Trp Lys Asp His Lys Ala Tyr
            580                 585                 590

Ile Asp Lys Glu Ile Glu Ala Leu Gln Asp Lys Ile Lys Asn Leu Arg
            595                 600                 605

Glu Val Arg Gly His Leu Lys Arg Arg Lys Pro Glu Glu Cys Ser Cys
            610                 615                 620

Ser Lys Gln Ser Tyr Tyr Asn Lys Glu Lys Gly Val Lys Lys Gln Glu
625                 630                 635                 640

Lys Leu Lys Ser His Leu His Pro Phe Lys Glu Ala Ala Gln Glu Val
                645                 650                 655

Asp Ser Lys Leu Gln Leu Phe Lys Glu Asn Asn Arg Arg Arg Lys Lys
            660                 665                 670

Glu Arg Lys Glu Lys Arg Gln Arg Lys Gly Glu Glu Cys Ser Leu
            675                 680                 685

Pro Gly Leu Thr Cys Phe Thr His Asp Asn Asn His Trp Gln Thr Ala
690                 695                 700

Pro Phe Trp Asn Leu Gly Ser Phe Cys Ala Cys Thr Ser Ser Asn Asn
705                 710                 715                 720

Asn Thr Tyr Trp Cys Leu Arg Thr Val Asn Glu Thr His Asn Phe Leu
                725                 730                 735

Phe Cys Glu Phe Ala Thr Gly Phe Leu Glu Tyr Phe Asp Met Asn Thr
            740                 745                 750

Asp Pro Tyr Gln Leu Thr Asn Thr Val His Thr Val Glu Arg Gly Ile
            755                 760                 765

Leu Asn Gln Leu His Val Gln Leu Met Glu Leu Arg Ser Cys Gln Gly
770                 775                 780

Tyr Lys Gln Cys Asn Pro Arg Pro Lys Asn Leu Asp Val Gly Asn Lys
785                 790                 795                 800

Asp Gly Gly Ser Tyr Asp Leu His Arg Gly Gln Leu Trp Asp Gly Trp
                805                 810                 815

Glu Gly Xaa Ser Ala Pro Ser His Cys Arg His Gln Leu Ala Arg Pro
            820                 825                 830

Arg Gly Ala Thr Gln Cys Glu Xaa Lys His Leu Xaa Val Gln Thr Lys
```

-continued

```
                835                 840                 845
Leu Gln Thr Xaa Ser Gly Gly Leu Asp Xaa Leu Leu Glu Gly Phe Arg
    850                 855                 860
Xaa Ser Ile Cys Thr Ala Glu Glu Ser Leu Xaa Ala Lys Xaa Asn Lys
865                 870                 875                 880
Xaa Asp Ser Asn Cys Ser Lys Xaa Arg Val Leu Gly Cys Leu Cys Xaa
                885                 890                 895
Ala Arg Cys Val Asn Gly Asp Gly Leu Cys Xaa Leu Arg Xaa Arg Pro
            900                 905                 910
Lys Ala Xaa Gly Trp Glu Asn Thr Ser Phe Asp Leu Ala Ser Xaa Pro
        915                 920                 925
Ser Asn Pro Ala Phe Glu Pro Thr Asn Ile Lys Ser Arg Glu Xaa Thr
    930                 935                 940
Xaa Met Glu Xaa Arg His Ser Arg Ser Xaa Ser Phe Glu Phe Xaa Thr
945                 950                 955                 960
Leu Glu Lys Asn Arg Lys Met Asp Gly Ala Xaa Arg Asp Xaa Ser Ser
                965                 970                 975
Gly Asn Arg Phe Gln Trp Arg Trp His Asp Arg Ala Arg Ala Arg Ala
            980                 985                 990
Gln Pro Gln Ala Ala Ala His Ser Gln Ala Pro Glu Arg Thr Ser Pro
        995                 1000                1005
Val Trp Trp Ser Trp Lys Gly His Phe Xaa Arg Ser Thr Ile Ser Ser
    1010                1015                1020
Cys Ala Phe Arg Trp Asn Phe Ser Ser Ser Asp Val His His Gly His
1025                1030                1035                1040
Arg Arg Thr Pro Lys Xaa Phe Gln His Ser Gly Glu Asp Val Asp Gln
                1045                1050                1055
Gly Gly Glu Glu Ser Arg Lys Gly Glu Val Thr Ala Pro Arg Arg Gln
            1060                1065                1070
Arg Leu Leu Phe Thr Leu Leu Xaa Leu Asp Glu Thr Val Thr Leu Pro
        1075                1080                1085
Xaa Thr Gln Tyr Phe Phe Leu Thr Phe Leu Phe Val Asn Xaa Xaa Arg
    1090                1095                1100
Xaa Ser Gln Pro Pro Thr Phe Gln Ala Thr Leu Gly Thr Phe Val Gln
1105                1110                1115                1120
Xaa Lys Leu Val Ser Met Xaa Ala Ser Gly Val His Thr Glu Thr His
                1125                1130                1135
Arg Tyr Asn Leu Leu Ser Ala Lys Ser Arg Lys Lys Gly Trp Gly Tyr
            1140                1145                1150
Leu Gly Trp Leu Gly Phe Asp Phe Leu Leu Val Cys Leu Phe Cys Thr
        1155                1160                1165
Lys Thr Val Leu Ser Phe Glu Tyr Arg Arg Asp Ile Ser Ile Tyr Met
    1170                1175                1180
Leu Ser Asn Gln Asp Gly Xaa Asn Gly Ala Phe Leu Ser Val Xaa Asn
1185                1190                1195                1200
Leu Thr Pro Leu Val Asn Leu Ser Thr His Phe His Cys Leu Arg Asn
                1205                1210                1215
Glu Val Leu Ile His Phe Xaa Pro Leu Glu Phe Phe Asn Ala Val Ile
            1220                1225                1230
Phe Ser Xaa Met Ile Leu His Phe Glu Ile Lys Met Pro Cys Leu Phe
        1235                1240                1245
Asp Xaa Ser Tyr Phe Phe Ile Phe Thr Gly Leu Ser Val Ser Leu Leu
    1250                1255                1260
```

Ala Val Ile Val Thr Lys Ser Asn Lys Pro Arg Thr Thr His Ser
1265                1270                1275                1280

Met Asp His Ile Leu Phe Asp Ile Lys Leu Leu Pro Glu Asn Val Ala
            1285                1290                1295

Cys Val Leu Pro Arg Leu Ala Lys Ile Asp Xaa Gln Lys Gly Met Ala
        1300                1305                1310

Asn Asn Val Gly Gly Glu Asn Lys Xaa Ile Ser Lys Gln Asn Glu Asp
    1315                1320                1325

Cys Leu Leu Ser Leu Cys Leu Ala Ser Lys Arg Ser Ser Tyr Ile Ile
1330                1335                1340

Pro Leu Arg Leu Leu Tyr Phe Gly Leu Phe Ser Xaa Gln Glu Lys Lys
1345                1350                1355                1360

Ile Xaa Arg Ser Phe Ile Phe Ile Phe Phe Gly Phe Leu Gly Met Thr
            1365                1370                1375

Lys Lys Leu Lys Cys Xaa Xaa Asn Met Thr Ser Phe Glu Phe Thr Pro
        1380                1385                1390

Arg Thr Ser Gln Xaa Lys Lys Ile Met Asn Ala Pro Gln Phe Gln His
    1395                1400                1405

Thr Thr Arg Glu Val Asn Phe Leu Thr Leu Cys Ser Met Ile Ile Cys
1410                1415                1420

Lys Thr Phe Thr Lys Phe Xaa Tyr Leu Leu Lys Thr Xaa Phe Lys Ile
1425                1430                1435                1440

Ala Phe Glu Asn Leu Tyr Ser Xaa Lys Tyr Pro Cys Cys Val Leu Gly
            1445                1450                1455

Phe Xaa Ile Pro Ala Lys Gly Leu Pro His Xaa Val Ile Ser Thr Leu
        1460                1465                1470

Leu Phe Ser Ser Pro Arg Xaa Cys Val Phe Ala Tyr Pro Lys Arg Gly
    1475                1480                1485

Phe Leu Leu Ile Phe Arg Xaa Phe Lys Cys Leu Asp Lys Leu Cys Phe
1490                1495                1500

Leu Xaa Val Phe Met Val Asn Ser Phe Lys Glu Asn Leu Ile Cys Tyr
1505                1510                1515                1520

Ser Xaa Ile Phe Leu Val Thr Leu Asn Leu Tyr His Arg Leu Cys Thr
            1525                1530                1535

Tyr Val Gln Ile Ser Cys Leu Pro Asp Val Cys Ile Ile Gly Gly Met
        1540                1545                1550

Thr Glu Gln Thr Tyr Leu Xaa Ser Xaa Ile Met Cys Phe Val Lys Arg
    1555                1560                1565

Phe Gln Val Ile Arg Lys His Thr Leu Phe Phe Asn His Val Xaa Tyr
1570                1575                1580

Ser Met Ile Leu Leu Xaa Asn Asn Ser Gly Phe Arg Lys Val Xaa Lys
1585                1590                1595                1600

Gln Tyr Phe Phe Lys Xaa Lys Val Phe Lys Leu
            1605                1610

<210> SEQ ID NO 17
<211> LENGTH: 590
<212> TYPE: DNA
<213> ORGANISM: Homo sapiens
<220> FEATURE:
<221> NAME/KEY: unsure
<222> LOCATION: (173)
<223> OTHER INFORMATION: a, c, g or t
<220> FEATURE:
<221> NAME/KEY: unsure
<222> LOCATION: (561)

```
<223> OTHER INFORMATION: a, c, g or t
<220> FEATURE:
<221> NAME/KEY: unsure
<222> LOCATION: (567)
<223> OTHER INFORMATION: a, c, g or t

<400> SEQUENCE: 17
cacctttctc tttattggaa tagctttgtt tactgcagct acattcctca ggcttccttc      60
tcttcagatg tcctctcact tctcttaaat tcttaatttt atcttgcaga gcttcaatct    120
ctttgtcaat gtatgcctta tggtccttcc acgctctggc cgattggtac agntctctct    180
cacaatggat agagtcattg ggaagaataa aacacttgtg tgtcactcgg acagtggtag    240
gtgggcccac ggcgttgctg ctatctgcca gcatcctgcc cctgttgcca ccactggaag    300
cctggagatc tcttggcccc ttgtggcctt catcatgacg cttagcaatg tttcttggtt    360
gcaacacttg caattcttct tcttcttcca gatttatgtc atatatttca ccttcaaatt    420
cgacggacaa ggaacgtgtc tgccgagtat ggacaaatct gggcttgtac tttggagtcc    480
cctggtttct caagaattgc cgttgactct ttctttggct tctgctggca cggtaaccag    540
actccctaca actgcactct ntgtctntgt catggaagcc gcgagcgtag                590

<210> SEQ ID NO 18
<211> LENGTH: 196
<212> TYPE: PRT
<213> ORGANISM: Homo sapiens
<220> FEATURE:
<221> NAME/KEY: UNSURE
<222> LOCATION: (8)
<223> OTHER INFORMATION: any amino acid
<220> FEATURE:
<221> NAME/KEY: UNSURE
<222> LOCATION: (10)
<223> OTHER INFORMATION: any amino acid
<220> FEATURE:
<221> NAME/KEY: UNSURE
<222> LOCATION: (139)
<223> OTHER INFORMATION: any amino acid

<400> SEQUENCE: 18

Tyr Ala Arg Gly Phe His Asp Xaa Asp Xaa Glu Cys Ser Cys Arg Glu
  1               5                  10                  15

Ser Gly Tyr Arg Ala Ser Arg Ser Gln Arg Lys Ser Gln Arg Gln Phe
             20                  25                  30

Leu Arg Asn Gln Gly Thr Pro Lys Tyr Lys Pro Arg Phe Val His Thr
         35                  40                  45

Arg Gln Thr Arg Ser Leu Ser Val Glu Phe Glu Gly Glu Ile Tyr Asp
     50                  55                  60

Ile Asn Leu Glu Glu Glu Glu Leu Gln Val Leu Gln Pro Arg Asn
 65                  70                  75                  80

Ile Ala Lys Arg His Asp Glu Gly His Lys Gly Pro Arg Asp Leu Gln
                 85                  90                  95

Ala Ser Ser Gly Gly Asn Arg Gly Arg Met Leu Ala Asp Ser Ser Asn
            100                 105                 110

Ala Val Gly Pro Pro Thr Thr Val Arg Val Thr His Lys Cys Phe Ile
        115                 120                 125

Leu Pro Asn Asp Ser Ile His Cys Glu Arg Xaa Leu Tyr Gln Ser Ala
    130                 135                 140

Arg Ala Trp Lys Asp His Lys Ala Tyr Ile Asp Lys Glu Ile Glu Ala
145                 150                 155                 160

Leu Gln Asp Lys Ile Lys Asn Leu Arg Glu Val Arg Gly His Leu Lys
```

```
                     165                 170                 175
Arg Arg Lys Pro Glu Glu Cys Ser Cys Ser Lys Gln Ser Tyr Ser Asn
            180                 185                 190

Lys Glu Lys Gly
        195

<210> SEQ ID NO 19
<211> LENGTH: 288
<212> TYPE: DNA
<213> ORGANISM: Homo sapiens
<220> FEATURE:
<221> NAME/KEY: unsure
<222> LOCATION: (35)
<223> OTHER INFORMATION: a, c, g or t
<220> FEATURE:
<221> NAME/KEY: unsure
<222> LOCATION: (108)
<223> OTHER INFORMATION: a, c, g or t
<220> FEATURE:
<221> NAME/KEY: unsure
<222> LOCATION: (170)
<223> OTHER INFORMATION: a, c, g or t
<220> FEATURE:
<221> NAME/KEY: unsure
<222> LOCATION: (195)..(196)
<223> OTHER INFORMATION: a, c, g or t
<220> FEATURE:
<221> NAME/KEY: unsure
<222> LOCATION: (233)..(234)
<223> OTHER INFORMATION: a, c, g or t

<400> SEQUENCE: 19
aagaaggaga ggaaggagaa gagacggcag aggangggggg aagagtgcag cctgcctggc      60
ctcacttgct tcacgcatga caacaaccac tggcagacag ccccgttntg gaacctggga     120
tctttctgtg cttgcacgag ttctaacaat aacacctact ggtgtttgcn tacagttaat     180
gagacgcata atttnntttt ctgtgagttt gctactggct ttttggagta ttnngatatg     240
aatacagatc cttatcagct cacaaataca gtgcacacgg ttagaacg                  288

<210> SEQ ID NO 20
<211> LENGTH: 96
<212> TYPE: PRT
<213> ORGANISM: Homo sapiens
<220> FEATURE:
<221> NAME/KEY: UNSURE
<222> LOCATION: (12)
<223> OTHER INFORMATION: any amino acid
<220> FEATURE:
<221> NAME/KEY: UNSURE
<222> LOCATION: (36)
<223> OTHER INFORMATION: any amino acid
<220> FEATURE:
<221> NAME/KEY: UNSURE
<222> LOCATION: (57)
<223> OTHER INFORMATION: any amino acid
<220> FEATURE:
<221> NAME/KEY: UNSURE
<222> LOCATION: (65)..(66)
<223> OTHER INFORMATION: any amino acid
<220> FEATURE:
<221> NAME/KEY: UNSURE
<222> LOCATION: (78)
<223> OTHER INFORMATION: any amino acid

<400> SEQUENCE: 20

Lys Lys Glu Arg Lys Glu Lys Arg Arg Gln Arg Xaa Gly Glu Glu Cys
  1               5                  10                  15

Ser Leu Pro Gly Leu Thr Cys Phe Thr His Asp Asn Asn His Trp Gln
             20                  25                  30
```

```
Thr Ala Pro Xaa Trp Asn Leu Gly Ser Phe Cys Ala Cys Thr Ser Ser
        35                  40                  45

Asn Asn Asn Thr Tyr Trp Cys Leu Xaa Thr Val Asn Glu Thr His Asn
     50                  55                  60

Xaa Xaa Phe Cys Glu Phe Ala Thr Gly Phe Leu Glu Tyr Xaa Asp Met
 65              70                  75                  80

Asn Thr Asp Pro Tyr Gln Leu Thr Asn Thr Val His Thr Val Arg Thr
             85                  90                  95
```

<210> SEQ ID NO 21
<211> LENGTH: 296
<212> TYPE: DNA
<213> ORGANISM: Homo sapiens
<220> FEATURE:
<221> NAME/KEY: unsure
<222> LOCATION: (84)
<223> OTHER INFORMATION: a, c, g or t
<220> FEATURE:
<221> NAME/KEY: unsure
<222> LOCATION: (159)
<223> OTHER INFORMATION: a, c, g or t
<220> FEATURE:
<221> NAME/KEY: unsure
<222> LOCATION: (184)
<223> OTHER INFORMATION: a, c, g or t
<220> FEATURE:
<221> NAME/KEY: unsure
<222> LOCATION: (234)
<223> OTHER INFORMATION: a, c, g or t
<220> FEATURE:
<221> NAME/KEY: unsure
<222> LOCATION: (238)
<223> OTHER INFORMATION: a, c, g or t

<400> SEQUENCE: 21

```
gtggcactgg aggccttccc gactactcag ccgccaaccc cattaaagtg acacatcggt      60
gctacatcct agagaacgac acantccagt gtgacctgga cctgtacaag tccctgcagg    120
cctggaaaga ccacaagctg cacatcgacc acgagattna aaccctgcag aacaaaatta    180 aganccctgag ggaagtccga ggtcacctga agaaaaagcg ccagaagaa tgtnactntc   240 acaaaatcag ctaccacacc cagcacaaag gccgcctcaa gcacagaggc tccagt        296
```

<210> SEQ ID NO 22
<211> LENGTH: 98
<212> TYPE: PRT
<213> ORGANISM: Homo sapiens
<220> FEATURE:
<221> NAME/KEY: UNSURE
<222> LOCATION: (28)
<223> OTHER INFORMATION: any amino acid
<220> FEATURE:
<221> NAME/KEY: UNSURE
<222> LOCATION: (53)
<223> OTHER INFORMATION: any amino acid
<220> FEATURE:
<221> NAME/KEY: UNSURE
<222> LOCATION: (61)
<223> OTHER INFORMATION: any amino acid
<220> FEATURE:
<221> NAME/KEY: UNSURE
<222> LOCATION: (78)..(79)
<223> OTHER INFORMATION: any amino acid

<400> SEQUENCE: 22

```
Gly Thr Gly Gly Leu Pro Asp Tyr Ser Ala Ala Asn Pro Ile Lys Val
 1               5                  10                  15

Thr His Arg Cys Tyr Ile Leu Glu Asn Asp Thr Xaa Gln Cys Asp Leu
```

-continued

```
                    20                  25                  30
Asp Leu Tyr Lys Ser Leu Gln Ala Trp Lys Asp His Lys Leu His Ile
            35                  40                  45

Asp His Glu Ile Xaa Thr Leu Gln Asn Lys Ile Lys Xaa Leu Arg Glu
        50                  55                  60

Val Arg Gly His Leu Lys Lys Lys Arg Pro Glu Glu Cys Xaa Xaa His
65                  70                  75                  80

Lys Ile Ser Tyr His Thr Gln His Lys Gly Arg Leu Lys His Arg Gly
                85                  90                  95

Ser Ser
```

IDENTIFICATION AND CLONING OF A NEW SUBFAMILY OF SULFATASES AND FUNCTIONAL EMBRYONIC TECHNIQUES FOR CHARACTERIZATION OF SUCH PROTEINS

INTRODUCTION

This application is a continuation of U.S. patent application Ser. No. 09/668,673 filed Sep. 22, 2000, now U.S. Pat. No. 6,562,956, which claims the benefit of priority from U.S. Provisional Application Serial No. 60/155,738, filed Sep. 23, 1999, each of which are herein incorporated by reference in their entirety.

This invention was supported in part by funds from the U.S. government (NIH Grant No. HD07796-27) and the U.S. government may therefore have certain rights in the invention.

BACKGROUND OF THE INVENTION

Glucosamine-6-sulfatase (G6S) is a lysosomal enzyme found in all cells. This exo-hydrolase is involved in the catabolism of heparin, heparin sulphate and keratin sulphate. Deficiencies in G6S result in the accumulation of undegraded substrate and the lysosomal storage disorder mucopolysaccharidosis type IIID.

Regional mapping by in situ hybridization of a $^3$H-labeled human G6S CDNA probe to human metaphase chromosomes indicated that the G6s gene is localized to chromosome 12 at q14. Localization to the G6S gene to chromosome 12 was confirmed via Southern blot hybridization analysis of DNA from human x mouse hybrid cell lines (Robertson et al. Hum. Genet. 1988 79(2):175–8).

Human liver contains two major active forms of glucosamine-6-sulfatase, form A which has a single 78 kDa polypeptide and form B which has two polypeptides of 48 kDa and 32 kDa. A 1761 base pair cDNA clone encoding the complete 48 kDa polypeptide of form B has been isolated (Robertson et al. Biochem. Biophys. Res. Commun. 1988 157(1):218–24). This sequence reveals homology with the microsomal enzyme steroid sulfatase. The amino acid sequence was also deduced from this human G6S clone (Robertson et al. Biochem. J. 1992 288(2):539–44). The predicted sequence has 552 amino acids with a leader peptide of 36 amino acids and contains 13 potential N-glycosylation sites, 10 of which are believed to be used. The derived amino acid sequence shows strong sequence similarity to other sulfatases such as the family of arylsulfatases.

SUMMARY OF THE INVENTION

The present invention relates to the identification and/or cloning of new, evolutionarily conserved members of a subfamily of sulfatases, referred to herein as Sulf-1 and Sulf-2, from quail embryos (QSulf-1), C. elegans (CeSulf-1), Drosophila melanogaster (DmSulf), mice (MSulf-1 and MSulf-2) and humans (HSulf-1 and HSulf-2).

The present invention also relates to Functional Embryonic Technologies (FETs) which serve as convenient and efficient embryo assays for the investigation and determination of the developmental functions of regulatory genes. Using FETs, members of this new family of sulfatases are demonstrated herein to be essential components of Sonic hedgehog (Shh) inductive signaling which is critical for the specification of neural and mesodermal lineages, as well as other lineages in the vertebrate embryo.

Thus, the present invention also relates to compositions and methods of using these compositions to modulate the expression and/or activity of proteins which are members of this subfamily of sulfatases to modify growth and differentiation of cells, as well as viral infection and inflammation. These methods are believed to be useful in the treatment of cancer, including metastases; in inducing differentiation of cells into myoblasts, neural cells and renal cells for use in the treatment of skeletomuscular degenerative diseases, neurodegenerative diseases and renal degenerative diseases; in inhibiting infection via viruses which utilize sulfated heparin proteoglycans for entry into cells; and in controlling the recruitment of lymphocytes by cells to a site of inflammation.

DETAILED DESCRIPTION OF THE INVENTION

Figure 1:
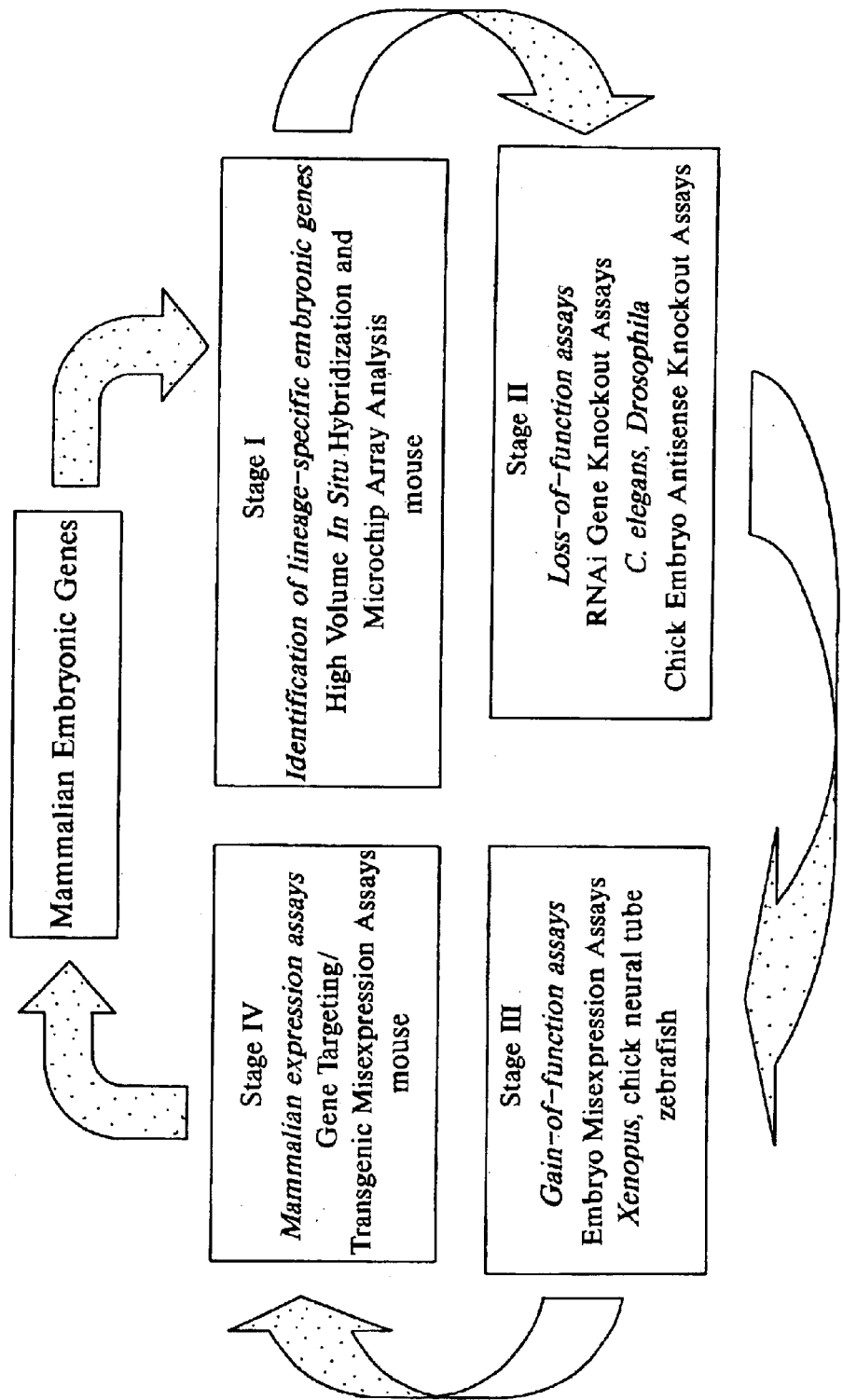
FIG. 1 provides a diagram of the four stages and assays used in each stage of functional embryonics technologies (FETs).

Functional Embryonics Technologies (FETs) is an efficient and cost-effective functional genomics strategy to investigate the developmental functions of novel mammalian genes in processes of stem cell specification, tissue differentiation, and organ formation. The FETs strategy combines differential molecular cloning techniques and bioinformatics analysis of genome databases with the use of simple, cost effective, and efficient bioassays in model embryos to identify genes with unique embryological, cellular and biochemical functions. It is believed that the majority of genes with important developmental regulatory and structural functions have not yet been discovered. There is ample evidence that many of the regulatory genes identified with lineage-specific expression in embryos are also regulators of stem cell production and differentiation, i.e., genes involved in building the differentiated tissues and organs in the embryo during development.

Many of the known genes that regulate embryonic development are conserved in animals, including C. elegans, Drosophila, Xenopus, chick, mouse, and human. Simple and efficient embryo bioassays are now available to identify the required functions of developmental regulatory genes in processes of stem cell specification, tissue differentiation and organogenesis, based on their dominant regulatory activities when misexpressed in embryos and in embryonic cells. In FETs, these methods are sequentially combined to identify novel regulatory genes having applications in the development of therapeutics for both stem cell production and tissue regeneration.

The starting point for FETs is the selection of a novel candidate regulatory or structural gene or set of genes for functional analysis. In one embodiment, candidate genes are identified through bioinformatic searches of the human or mouse genome and/or EST databases based on their significant gene family relationships, their evolutionary conservation with C. elegans and Drosophila genes, or their protein domain motifs. In another embodiment, directed specifically towards identification of genes with developmental functions, molecular technologies are used to define tissue-specific or developmentally-related sets of expressed genes. Examples of such molecular technologies include, but are not limited to, DNA microchip arrays, in situ hybridization, and/or subtractive cDNA cloning techniques, in combination with genome data base analysis. Once candidate genes of interest have been identified, their developmental functional activities are accessed through a series of rapid and cost-effective FETs assays, as presented in FIG. 1.

In Stage I, candidate genes with lineage-specific expression are identified by high volume in situ hybridization and microchip array assays. Stage II and III assays are directed towards identification of genes with activities that control early developmental processes in the embryo: cell lineage specification, proliferation, apoptosis, and the initiation of cell differentiation. Stage II RNAi gene knockout assays define the essential requirements of mammalian homologues of *C. elegans* and/or Drosophila genes in developing embryos. Antisense knockout assays can also be performed in chick embryos in Stage II to define the essential requirement of avian homologues. Stage III mRNA misexpression assays define the regulatory capacities of specific genes to dominantly direct developmental processes in vertebrate embryos. These Stage II and III assays also provide an opportunity to investigate the functional interactions of candidate genes with known genes in specific developmental pathways including Hedgehog, Wnt, BMP, FGF, and EGF pathways. Stage IV assays utilize DNA transfection in cell cultures to misexpress cDNAs of candidate genes in selected stem cell lines and transgenic mice, and loss-of-function gene targeting analysis to investigate cell biological functions of candidate genes in mammalian embryos. Stage II and III assays provide simple and efficient screens to identify candidate genes for analysis in mouse embryos by gene targeting and transgenesis, as well as for detailed functional studies in model embryos.

As shown in FIG. 1, in Stage II loss of function is determined via Embryo RNAi Gene Knockout Assays and/or Chick Embryo Antisense Knockout Assays. The *C. elegans* genome sequence is complete, and the Drosophila genome sequence will be completed in the near future, making possible the identification of homologues of mammalian genes in *C. elegans* and Drosophila. Homologues of mouse genes can be functionally disrupted in embryos by RNAi technology, which involves microinjection of double-stranded RNA of transcribed regions of the candidate homologue genes into gonads or early embryos (Kennerdell, J. R. and Carthew, R. W. Cell 1998 95(7):1017–26; Misquitta, L. and Paterson, B. M. Proc. Natl Acad. Sci. USA 1999 96(4):1451–6). Double stranded RNAs are routinely produced by PCR amplification of genomic DNA, using primers derived from sequence databases, and cloned into expression vectors for RNA production. Double stranded RNAs of partially transcribed sequences are sufficient for RNAi gene knockout, and multiple genes can be inactivated simultaneously to characterize genes with redundant functions. RNAi causes germline disruptions of gene function in *C. elegans*. Analysis to define mutant phenotypes is effectively performed on living or fixed embryos using DIC and fluorescence microscopy because of the limited cell numbers in these embryos. GFP reporter genes are available to monitor cell lineage specification, tissue differentiation and organ formation. Phenotypic assays can be tailored to monitor specific developmental pathways using specific reporter and genetic backgrounds. RNAi assays can be accomplished rapidly in a time frame of days and weeks and can be expected to identify genes with essential regulatory and structural functions for more detailed genetic and molecular studies in these organisms as well as for Stage II analysis. Similarly, chick embryo antisense knockout assays are fast assays which, as shown herein, are useful in identifying genes with essential and structural functions in avian embryos.

In Stage III, gain of function is determined via Embryo Misexpression Assays in Xenopus, chick neural tube and zebrafish. The Xenopus egg is ideally suited for misexpression and overexpression of candidate genes, by microinjection of mRNA or cDNA expression plasmids into blastomeres of newly fertilized eggs (Thomsen, G. H. and Melton, D. A. Cell 1993 74(3):433–41). Full length cDNAs are recovered by PCR amplification of mouse embryo cDNA libraries using primers to sequences derived from genomic and EST data bases. Xenopus microinjection assays are performed on candidate mouse and human RNAs whose homologues have functional activities in Stage II assays or on candidates that do not have recognized *C. elegans* and Drosophila homologues. Xenopus misexpression assays are performed on pools of multiple RNAs candidates, allowing for high through-put assays on groups of mRNAs. Histological, marker, and reporter gene expression phenotypes are used to monitor regulatory activities in well-established assays. Dominant mutant receptors, signaling components and transcription factors are available, making possible co-expression studies to investigate gene interactions with known developmental pathways. Xenopus misexpression assays can be accomplished in a time frame of days and identify regulatory genes that control early developmental cell lineage specification and differentiation.

Chick Neural Tube Electroporation is also performed. The chick embryo is utilized to investigate the functions of candidate EEA cDNAs by neural tube electroporation (Sakamoto et al. FEBS Letters 1998 426(3):337–41). Electroporation is a technically simple and highly efficient method for transfecting primitive neural tube cells with cDNA expression vectors to misexpress candidate mRNAs. Histological and reporter gene assays are used to determine the effects of misexpression on signal transduction and cell differentiation processes in the neural tube. Chick assays can be accomplished in a time frame of days and identify regulatory and structural genes that control processes of developmental signaling and patterning, axon guidance, and neuronal cell differentiation.

Zebrafish Microinjections are also performed. Mutations that disrupt a large number of specific developmental processes have been identified in Zebrafish, making possible functional interaction studies with candidate genes as well as misexpression assays in wild type embryos (Westerfield, 1995 *The Zebrafish Book*. University of Oregon Press). These assays involve mRNA injection into embryonic blastomeres and histological and reporter gene assays. The Zebrafish embryo develops rapidly, and the embryo is transparent and small, so it is possible to evaluate cellular processes at high resolution to identify RNAs with regulatory and structural functions. RNA injections are technically more demanding and less efficient in the Zebrafish than in Xenopus, but can be accomplished in a time frame of days.

In Stage IV, genes with in Stage II-III assays are selected for mammalian expression assays via mouse gene targeting and transgenic studies. Gene targeting is technically demanding, expensive and requires a substantial commitment of time (one year), but is essential to determine the loss-of-function embryonic phenotypes, which will be evident if the gene of interest is not a redundant gene or is not active in a parallel pathway (Hogan et al. *Manipulating the Mouse Embryo: A Laboratory Manual*. 1994 New York, Cold Spring Harbor Laboratory Press, 2nd Edition). Once the mouse genome is sequences, however, the cloning procedures required for gene targeting will be simplified. RNAi technology or an equivalent also may be available to provide more highly efficient procedures for producing mouse mutants. Candidate cDNAs under the control of UAS promoters and these promoters themselves will be misexpressed in different tissues of developing embryos using lines of mice engineered with tissue-specific transgenes to produce GAL4, a UAS transcriptional activating protein. These studies identify dominant regulatory activities of candidate genes. An increasing number of GAL4 lines of mice are being generated, making possible conditional misexpression of candidate cDNAs in the mouse embryo. Transient transgenic assays are preferable and can be accomplished in a matter of several weeks. Production of germline transgenics is technically demanding and costly; assays involve production of transgenic mice lines, which requires 4–6 months.

FETS were used to functionally characterize members of the new Sulf-1 and Sulf-2 sulfatase gene subfamily.

QSulf-1 was cloned from newly formed somites of quail embryos by differential display technology as described by Liang, P. and Pardee, A. B. (Science 1992 257:967–971). It was found that somite formation in vertebrate embryos is coordinated with the activation of master regulatory gene including the transcription factor genes Pax1 and MyoD/Myf5, which are essential for the determination of sclerotome cartilage and myotomal muscle lineages, respectively. Differential display experiments were therefore directed to identify additional genes that are activated during somite formation as candidates for other genes in the sclerotome and myotome lineage determination pathways. The screen involved assaying for cDNA copies of mRNA transcripts that are present in the three newest born somites at the posterior edge of somite formation in stage 12 embryos, but are absent in the presegmented mesoderm immediately posterior to these somites. As somite pairs are born in quail embryos every 90 minutes, the window of gene expression being investigated in these studies is approximately 4.5 hours, thus allowing recovery of "immediate early" somite response genes. A number of somite-specific, differentially displayed transcripts were identified in these studies and clones were sequenced. However, because the differential display strategy recovers cDNAs that encode only small sequence intervals restricted largely to the 3' untranslated regions, these sequences are generally not informative regarding encoded proteins.

Thus, to identify clones of interest for further analysis, differential display clones were used as in situ hybridization probes and RT-PCR primers to assay expression in somites and presegmental mesoderm of stage 12 somites. Clones that showed expression in somites, but not presegmental mesoderm met the criteria for the screen. Clones were chosen for further analysis based on confirmation of their patterned expression in the somite. Specifically, clones of transcripts were identified in the ventral somite, which gives rise to the sclerotome lineages, and/or the dorsal medal somite, which gives rise to the epaxial myotomal lineages.

The QSulf-1 cDNA hybridized to transcripts that were activated during somite formation, initially in the ventral, sclerotomal lineage and then in the more dorsal myotomal lineage. Expression also occurred in the notochord, the neural tube floor plate, in interneurons and other sites. The full length CDNA of QSulf-1 and the translated protein sequence of QSulf-1 are depicted in SEQ ID NO:1 and SEQ ID NO:2, respectively.

Based upon these experiments, the full length CDNA clone of QSulf-1 was recovered by screening a stage 12 quail cDNA library with the QSulf-1 probe. These full length clones have extensive 5' and 3' UTR sequences and the library was directionally cloned in a vector that includes a CMV promoter, to allow immediate transfection studies.

Sequence and computer database analyses of the quail, full-length Sulf-1 cDNA revealed the open reading frame to have homology with sulfatases in other species. For example, the QSulf-1 sequence was closely related to the cDNA of human glucosamine-6-sulfatase (Robertson et al. Biochem. J. 1992 288:539–544). A related protein, referred to herein as CeSulf-1, was also identified by Gene Finder in the C. elegans database. The CeSulf-1 protein translated from cosmid CELKO9C4 is depicted herein as SEQ ID NO:3. In addition, two Drosophila ESTs AA391898 (SEQ ID NO:4) and AA438825 (SEQ ID NO:5) have been identified as clones for a Drosophila sulfatase (DmSulf) based upon their close relationship to CeSulf-1 and QSulf-1. These ESTs have been demonstrated to be expressed in early mesodermal cells that give rise to muscles in Drosophila similar to QSulf-1 in quail. A mouse EST A1592342 (SEQ ID NO:6) has also been identified as a clone for a murine sulfatase (MSulf-1) along with a human cDNA AB029000 (SEQ ID NO:15; Kikuno et al. DNA Res. 1999 6:197–205) and human ESTs and proteins translated from human ESTs AI344026 (SEQ ID NO:17 and SEQ ID NO:18; Adams et al. Nature 1995 377(6547): 3–174), and AA361498 (SEQ ID NO:19 and SEQ ID NO:20; Adams et al. Nature 1995 377(6547): 3–174) for human sulfatase (HSulf-1) based upon their close relationship to CeSulf-1 and QSulf-1. The protein translated from MEST A1592342 is depicted in SEQ ID NO:7. The protein translated from HSulf-1 AB029000 is depicted in SEQ ID NO:16.

A second member of this sulfatase subfamily, referred to herein as Sulf-2, was also identified in mouse (MSulf-2) and human (HSulf-2) based upon its close, but distinct, sequence relationship to QSulf-1, MSulf-1 and HSulf-1. MSulf-2 MEST AA015479 is depicted in SEQ ID NO:8; MSulf-2 MEST AA138508 is depicted in SEQ ID NO:9; MSulf-2 MEST AA461855 is depicted in SEQ ID NO:10; MSulf-2 MEST AA727360 is depicted in SEQ ID NO:11; and MSulf-2 MEST W97878 is depicted in SEQ ID NO:12. The contig of these MSulf-2 ESTs is depicted in SEQ ID NO:13 and the translated protein of the contig of Msulf-2 ESTs is depicted in SEQ ID NO:14. HSulf-2 HEST AA323130 and the translated protein of this HSulf-2 EST are depicted in SEQ ID NO: 21 and 22, respectively. Further MSulf-2 is expressed in somites and neural cells as is MSulf-1 and QSulf-1. However, expression studies using in situ hybridization methods have shown that mouse MSulf-1 and MSulf-2 are expressed differentially in tissues of early mouse embryos. MSulf-1 is expressed in dermomyotome and dorsal neural tube lineages, whereas MSulf-2 is expressed in more ventral sclerotome and ventral neural tube lineages. Accordingly, both MSulf-1 and MSulf-2 are believed to have functions in the differentiation of different tissues and organs in the embryo.

The active site of the sulfatase enzyme is located in the N-terminal 200 amino acids. Conservation of amino acid residues in this enzymatic active site domain in Sulf-1 and Sulf-2 proteins from all species studied define this gene subfamily as functional sulfatases. The Sulf-1 and Sulf-2 proteins are clearly different from human G6S and the arylsulfatases described previously in the art.

In situ hybridization analysis revealed that the expression of QSulf-1 is temporally regulated and spatially patterned in the quail embryos. The striking patterns of expression observed indicate QSulf-1 to have lineage-specific functions in the quail embryo. Specifically, QSulf-1 is activated in somites following somite formation, in a progression that parallels MyoD activation. In early embryos prior to 10 somite pairs, somites do not express detectable QSulf-1. Expression becomes active and coordinated with somite formation in embryos with 10 to 15 somite pairs. Initially, expression is detected in the ventral medial somite, where Pax1 is activated and the sclerotome lineage is derived. Expression becomes dorsalized during somite maturation, localizing expression to the dorsal medial region of MyoD/Myf5 activation and formation of the myotome lineage. Expression does not extend into the dermyotome, but rather is restricted to cells immediately ventral. These cells are believed to comprise the developing myotomal muscle. Expression in the notochord is earlier than in somites and follows an anterior to posterior progression in the region of somite formation. Expression does not occur in the notochord adjacent to presegmental mesoderm. Expression is activated in the floorplate in coordination with floor plate differentiation, which occurs anterior to the zone of somite formation. Expression is observed somewhat later in the interneuron region of the neural tube. QSulf-1 is expressed specifically in the mesonephros and nephros, but not in the duct. Expression in the brain and limb bud also is highly localized and patterned.

Using surgical manipulations as described by Pownall et al. (Development 1996 122:1475–1488), it was found that QSulf-1 is an Shh-dependent somite gene. Specifically, it was found that the notochord is required for somite expression. Further, the lateral mesoderm is required to maintain lateral expression. The notochord requirement is believed to be due to Sonic hedgehog signaling since antisense inhibition of Shh was found to block the activation of QSulf-1 as it does the activation of MyoD and Myf5 in the epaxial myotomal lineage and Pax1 in the sclerotome lineage (Borycki et al. Development 1998 125:777–790). Antisense Shh also diminishes QSulf-1 expression in the floorplate and notochord as well as the mesonephros. Lateral plate mesoderm is known to mediate repression of MyoD and Myf5 through BMP4. This is also believed to be the repressive signal that maintains QSulf-1 expression in the medial somite.

Phosphothiolated antisense oligonucleotides were developed to inhibit expression of QSulf-1. When embryos were treated with these specific antisense oligonucleotides, expression of MyoD was specifically blocked in somites that are in the process of activating MyoD as well as in somites that are maintaining expression. Since Shh is required to activate and maintain epaxial myotome expression of MyoD and Myf5 in quail and mouse, it is believed that QSulf-1 has an essential function for MyoD/Myf5 activation downstream of the Shh signal. Thus, the role of QSulf-1 in Shh signaling is restricted to its sites of expression within the larger Shh response domain.

The structure, regulation and functional roles of this new subfamily of sulfatases determined through these experiments indicate members of this family such as Sulf-1 and Sulf-2 to act as either direct regulators of Shh diffusion from their notochord source of synthesis or as mediators of secondary signals such as FGF and Wnts with relay functions in gene regulation. Because of the close homology to the human G6S gene, it is believed that the function of Sulf-1 and Sulf-2 is related to a similar sulfatase activity to G6S which cleaves linked sulfate groups at the 6 position of the non-reducing glucosamine residues of heparin sulfate and keratin sulfate. Since QSulf-1 has been found to be regulated by Shh and is essential for its functions to mediate MyoD and Myf5 activation, this gene is also believed to function in the Shh pathway, directly or in a relay, and not in a parallel pathway. Further, since its expression is highly patterned in a subset of domains that are Shh responsive in the neural tube and somites, as well as the brain and limb, it is believed to have lineage-restricted functions related to the localized expression. The hydrophobic domain of its N-terminus is indicative of it functioning on the cell surface or being secreted to promote the localized desulfanation of heparin sulfanate proteoglycans in the ECM in the region of ECM of cells expressing the somite neural tube, brain, limb and mesonephros.

To investigate the secretion properties of QSulf-1, an expression vector encoding QSulf-1 with a C-terminal myc tag sequence was transfected into mammalian cells in culture and electroporated into neural tube of the developing chick embryo. Expressed QSulf-1 can then be localized by Western blotting methods as well as immunostaining using myc antibodies. It was found that QSulf-1 localized to the cell surface, where it was bound but not released freely into the extracellular space. Expressed QSulf-1 with a substituted collapsin N-terminal signal peptide also localized to the cell surface, thus providing further evidence that the sulfatase is secreted, but then binds to a component of the cells surface. Accordingly, QSulf-1 is the first known extracellular sulfatase, as all previously described sulfatases are lysosomal and involved in sulfate catabolism. The localization of QSulf-1 to the cell surface places this enzyme in proximity to its putative heparin sulfate proteoglycan (HSP) substrates, glypican and syndecan. As the sulfation state of glucosamine 6-sulfate on these HSP substrates regulates developmental signaling, this localization is consistent with other evidence provided herein that QSulf-1 has regulatory functions in the control of developmental signaling through its activity to regulate the sulfation states of glucosamine 6-sulfates on extracellular molecules such as HSP substrates.

A similar antisense approach to that described for somites can be used to better characterize QSulf-1 function in the neural tube floor plate and the notochord where QSulf-1 is expressed. In these experiments, embryos are treated with antisense QSulf-1 and expression of notochord, floor plate, motor neuron and interneuron-specific marker gene (Roelink et al. Cell 1994 76:761–775) is assayed. Pax3 is used as a marker to monitor the global changes in dorsal ventral neural tube patterning. Similar observations to somites treated with antisense QSulf-1 are expected as specific genes whose function is lost in response to QSulf-1 antisense treatment will be identified. Since QSulf-1 may regulate FGF activity to control the transition of somite cells from cell proliferation to differentiation, portions of premature differentiation in response to antisense QSulf-1 will also be monitored via an assay using differentiation markers over a time course treatment and inhibition of cell proliferation determined via BrdU incorporation and PCNA immunostaining.

To complement antisense experiments, QSulf-1 can also be misexpressed in the neural tube at various levels along the AP axis of the developing quail embryo using electroporation technology. In these experiments, QSulf-1 DNA and a control GFP expression plasmid are microinjected into the canal of the neural tube, which is then subjected to a brief electroporation shock to allow uptake of DNA. Embryos are then cultured at various times from 6 to 24 hours, thereby allowing time for overexpression of QSulf-1 at positions along the dorsal ventral axis of the neural tube in the region of the injection. This region of injection is varied relative to expression of endogenous QSulf-1. Embryos successfully electroporated are then fixed for in situ and antibody analysis. Notochord and neural tube markers of gene expression used in the antisense experiments are used to monitor gene expression. BrdU incorporation and PCNA immunostaining are used to monitor cell proliferation. C-terminal fusions of SdQSulf-1 with GFP in expression vectors can also be constructed for electroporation into neural tube and for transfection into cultured cells. GFP constructs permit monitoring of QSulf-1 expression directly, as well as determination of subcellular localization in membranes and possible secretion. The molecular expression phenotypes in response to overexpression to define the timing and patterning of neural differentiation provides complementary information to that obtained from the antisense experiments.

RT-PCR and RNases protection assays are also used to examine the expression of Sulf-1 in cultured quail myoblasts and the mammalian C2C12 myoblast cell line during the transition from cell proliferation to myofiber differentiation. In addition myoblasts can be transfected with Sulf-1 expression constructs in transient and stable assays to determine if overexpression enhances myoblast differentiation and/or changes the responsiveness of the cells to addition of FGF in the stimulation of proliferation and inhibition of differentiation. Mouse ESTs for Sulf-1 and Sulf-2 have been recovered from cultured myoblasts, thus indicating that members of this sulfatase subfamily are also expressed in murine myoblasts.

Xenopus embryos differentially utilize Shh, Wnt and FGF signaling pathways in the control of axis determination and mesoderm, endoderm and ectoderm cell specification (Heasman, J. Development 1997 124:4179–4191 and Pownall et al. Development 1996 122:3881–3892). A variety of molecular markers and morphological phenotypes are available to monitor these processes in overexpression of specific gene products by injection of in vitro transcribed mRNAs into newly fertilized embryos. Importantly, each of these signaling pathways can be distinguished by a unique combination of well-described perturbations in molecular and morphological phenotypes. For these experiments, Sulf-1 or Sulf-2 RNA is microinjected into blastomeres of newly fertilized embryos. These embryos are then allowed to undergo embryonic development. Injected embryos are assayed for abnormalities in body plan morphology and tissue histology, as well as for the misexpression of key marker genes that are characteristic of specific signaling pathways. For example, if overexpression of Sulf-1 or Sulf-2 interferes with FGF signaling, loss of tail mesoderm development and loss of myoD and Brachyury expression in injected embryos would be expected. Enhancement of FGF signaling would cause loss of head structures, gain of tail mesoderm, and increased myoD and Brachyury expression. If injected Sulf-1 or Sulf-2 enhances maternal Wnt signaling, duplication of axis phenotypes, increased Siamosis, which is a primary target of Wnt signaling, would be observed. Enhancement of zygotic Wnt signaling results in loss of head specification, gain of tail formation and increase in MyoD expression while loss of zygotic Wnt signaling results in loss of tail formation and MyoD expression. Enhancement of Shh signaling results in increased expression of floorplate and myogenic specification markers such as HNF3β, and MyoD, while loss of Hedgehog signaling has the opposite molecular phenotype as well as causing cyclopecia in embryos (Altaba, A. R. Development 1998 125:2203–2212).

In addition, since the C. elegans genome sequence is nearly complete, C. elegans homologues of vertebrate genes and related ESTs can be readily identified by computer analysis. In fact, the CeSulf-1 homologue was identified in the worm genome database and is depicted in SEQ ID NO:3.

Based on the expression of QSulf-1 in quail embryos, and the homology of this gene to Sulf-1 and/or Sulf-2 identified in C. elegans, Drosophila, mouse and human, it is believed that Sulf-1 and Sulf-2 are expressed in neural and muscle lineages in various species.

In C. elegans, the expression of any cloned gene can be readily disrupted for developmental analysis using RNAi technology. The RNAi procedure involves microinjection of double-stranded RNA in the coding region of the candidate genes into the oviduct and analysis of the phenotypes in emerging embryos. CeSulf-1 mutants can thus be generated in C. elegans by RNAi and by screening insertion mutant libraries for Sulf-1 mutants. RNAi and insertion mutant strains can be characterized for lineage-specific lesions in early developmental processes, which can be assessed by microscopic analysis and analysis of gene expression using in situ hybridization and antibody markers. Of specific interest are CeSulf-1 resulting in phenocopy loss-of function mutations of FGF, Wnt and Hedgehog signaling and lesions in neural and muscle lineages. For example, assays can be performed to determine whether CeSulf-1 is required for CeMyoD expression and myogenesis as demonstrated in quail embryo somites. Also, since FGF signaling in C. elegans is required for the migration and proper position of sex myoblasts (Burdine et al. Development 1998 125:1083–1093), this can also be examined in the CeSulf-1 mutant strains. Wnt signaling is required for neuroectoblast lineage determination and for the polarity of asymmetric cell division in tail hypodermal cells (Jiang, L. I. and Sternberg, P. W. Development 1998 125:2337–2347).

Based upon the activities demonstrated herein for members of this new sulfatase subfamily, it is believed that modulation of the expression and/or activity of proteins in this sulfatase family, such as Sulf-1 and Sulf-2, can be used to modify growth properties and differentiation of cells in various species including humans. Modulation of growth properties of cells through alteration of Sulf-1 or Sulf-2 levels or activity is expected to be useful in treatment of cancer and in the inhibition of metastases. Modulation of sulfatase levels and/or activity is also useful in promoting differentiation of stem cells into myoblasts, neural cells and renal cells. Accordingly, modulation of members of this new sulfatase subfamily is also expected to be useful in developing cells for transplant in the treatment of muscle degenerative diseases, neurodegenerative disease and renal degenerative disease and in initiation growth of healthy cells and healing diseased cells in these conditions. By "modulation" it is meant to increase or decrease levels or activity of proteins which are members of this subfamily of sulfatases, preferably Sulf-1 or Sulf-2. For example, the presence of a signal peptide in these proteins is indicative of their secretion. Accordingly, to increase protein levels, a gene encoding a member of this sulfatase subfamily can be administered via well known gene therapy methods. Alternatively, levels of the sulfatase can be increased by administration of a composition comprising purified, isolated sulfatase protein. Activity of this protein can be increased by administering an agonist designed to target and activate the sulfatase enzyme. Levels of expression of the sulfatase protein can be decreased by administration of an antisense oligonucleotide designed to hybridize with the sulfatase gene, thereby inhibiting its expression. Activity of the sulfatase protein can be decreased by administering an antagonist designed to target and inhibit activity of the sulfatase enzyme.

Further, it is believed that the extracellular glucose 6 sulfatases, Sulf-1 and Sulf-2, will be useful in the inhibition of viral infection and the control of inflammation. It is known that viruses such as Herpes Simplex virus and HIV-1 utilize sulfated heparin proteoglycans for viral entry (Shukla et al. Cell 1999 99:13; Banks et al. J. Cell Science 1998 111:533). Accordingly, modulating, or more preferably increasing, levels and/or activity of the extracellular glucose 6 sulfatases of the present invention, Sulf-1 and Sulf-2, via administration of purified enzymes or agents which increase levels or activity of these enzymes inhibits viral entry via sulfated heparin proteoglycans thereby inhibiting viral infection. Viral infections which can be inhibited via modulation of Sulf-1 and Sulf-2 are those caused by viruses which utilize sulfated heparin proteoglycans for viral entry. Similarly, it is known that cell surface glycosaminoglycans, including heparin sulfate proteoglycans, bind to cytokines to recruit lymphocytes to sites of inflammation (Kuschert et al. Biochemistry 1999 38:12959). The lectin-like receptor, L-selectin, also mediates rolling of lymphocytes on endothelial venules through interactions with sulfated glycosaminoglycans, including glucoaminoglycans and galacrosaminoglycans (Bistrup et al. J. Cell. Biol. 1999 145:899). Accordingly, extracellular glucose 6 sulfatases, Sulf-1 and Sulf-2, of the present invention or agents which modulate Sulf-1 or Sulf-2 activity or levels may also be used to control inflammation through modulation of lymphocyte recruitment.

What is claimed is:

1. An isolated nucleic acid sequence encoding a human sulfatase-2 protein coinprising SEQ ID NO:22.

2. The nucleic acid sequence of claim 1 comprising SEQ ID NO:21.

* * * * *